US007132406B2

(12) United States Patent
Kil et al.

(10) Patent No.: US 7,132,406 B2
(45) Date of Patent: *Nov. 7, 2006

(54) STIMULATION OF CELLULAR REGENERATION AND DIFFERENTIATION IN THE INNER EAR

(75) Inventors: Jonathan Kil, Seattle, WA (US); Hubert Lowenheim, Tubingen (DE); Rende Gu, Seattle, WA (US); Corinne Grigeur, Seattle, WA (US)

(73) Assignee: Sound Pharmaceuticals Incorporated, Seattle, WA (US)

( * ) Notice: Subject to any disclaimer, the term of this patent is extended or adjusted under 35 U.S.C. 154(b) by 247 days.

This patent is subject to a terminal disclaimer.

(21) Appl. No.: 10/458,108

(22) Filed: Jun. 9, 2003

(65) Prior Publication Data
US 2003/0203482 A1 Oct. 30, 2003

Related U.S. Application Data

(63) Continuation of application No. 09/614,099, filed on Jul. 11, 2000, now abandoned, which is a continuation-in-part of application No. PCT/US00/05736, filed on Mar. 3, 2000, and a continuation-in-part of application No. PCT/EP99/01153, filed on Feb. 23, 1999.

(51) Int. Cl.
A61K 48/00 (2006.01)
A61K 39/395 (2006.01)
(52) U.S. Cl. ..................... 514/44; 530/388.5
(58) Field of Classification Search ............... 514/44; 424/93.2; 530/388.5
See application file for complete search history.

(56) References Cited

U.S. PATENT DOCUMENTS

| 5,437,998 | A | 8/1995 | Schwarz et al. |
| 5,702,941 | A | 12/1997 | Schwarz |
| 5,763,279 | A | 6/1998 | Schwarz et al. |
| 5,770,580 | A * | 6/1998 | Ledley et al. ............... 514/44 |
| 6,066,652 | A | 5/2000 | Zenner et al. |
| 6,589,505 | B1 * | 7/2003 | Roussel et al. ............. 424/9.2 |

FOREIGN PATENT DOCUMENTS

| WO | WO 97/04762 A1 | 1/1997 |
| WO | WO 00/23084 A | 4/2000 |

OTHER PUBLICATIONS

Branch TIBS 23: 45-49, 1998.*
Gewirtz et al. PNAS, 93:3161-3163, 1996.*
Braasch et al., Biochemistry, 41:-4503-4510, 2002.*
Agrawal et al. TIBTECH 14:376-387,1996.*
Tamm et al. The Lancet 358:489-97 ,2001.*
Anderson, W.F., "Human Gene Therapy," Nature 392:25-30, 1998.
Birnbaum, J.E., et al., "Effects of Reserpine, Epidermal Growth Factor, and Cyclic Nucleotide Modulators on Epidermal Mitosis," Journal of Investigative Dermatology 66(05):313-318, 1976 (ACS Abstract No. 85:13565).
Chan, F.K.M., et al., "Identification of Human and Mouse p19, a Novel CDK4 and CDK6 Inhibitor with Homology to—16$^{ink4}$," Mol. Cell. Biol. 15(5):2682-2688, 1995.
Chardin, S., et al., "Regeneration and Mammalian Auditory Hair Cells," Science 267:707-711, 1995.
Chen, P., and N. Segil, "p27$^{Kip1}$ Links Cell Proliferation to Morphogenesis in the Developing Organ of Corti," Development 126:1581-1590, 1999.
Chiu, T.-L., and R.A. Goldstein, "Optimizing Energy Potentials for Success in Protein Tertiary Structure Prediction," Folding and Design 3:223-228, 1998.
Coats, S., et al., "Requirement of p27$^{Kip1}$ for Restriction Point Control of the Fibroblast Cell Cycle," Science 272:877-880, 1996.
Collum, R.G., et al., "A novel POU Homeodomain Gene Specifically Expressed in Cells of the Developing Mammalian Nervous System," Nucleic Acids Research (Abstract only) 20(18):4919-4925, 1992.
Cremers, F.P.M., Mapping and Cloning Hereditary Deafness Genes, Current Opinions in Genetics and Development 5:371-375, 1995.
Dal Bo, A., and A. Pitotti, "The Effects of β-Lactoglobulin Genetic Variants A and B on the Functional Properties of Whey Under Different Conditions," Food Hydrocolloids 11(1):41-48, 1997 (BIOSIS Abstract No. 1997:408589).
d'Aldin, C., et al., "Antisense Oligonucleotides to the GluR2 AMPA Receptor Subunit Modify Excitory Synaptic Transmission In Vivo," Mol. Brain Res. 55:151-164, 1998.
Dao, M.A., et al., "Reduction in Levels of the Cyclin-Dependent Kinase Inhibitor p27kip-1 Coupled With Transforming Growth Factor β Neutralization Induces Cell-Cycle Entry and Increases Retroviral Transduction of Primitive Human Hematopoietic Cells," Proc. Nat'l Acad. Sci. USA 95:13006-13011, 1998.
de Kok, Y.J.M., et al., "The Molecular Basis of X-Linked Deafness Type 3 (DFN3) in Two Sporadic Cases: Identification of Somatic Mosaicism for a POU3F4 Missense Mutation," Human Mutations 10:207-211, 1997.
El-Deiry, W.S., et al., "WAF1, A Potential Mediator of p53 Tumor Suppression," Cell 75(4):817-825, 1993.
Erber, R., et al., "Abberrant p21-CIP1/WAF1 Protein Accumulation in Head-and-Neck Cancer," Int'l Journal of Cancer 74(4):383-389, 1997.
Erkman, L., et al., "Role of Transcription Factors BRN-3.1 and Brn-3.2 in Auditory and Visual System Development," Nature 381(6583):603-606, 1996.
Gerrero, M.R., et al., "Brn-3.0: A POU-Domain Protein Expressed in the Sensory, Immune, and Endocrine Systems That Functions on Elements Distinct From Known Octamer Motifs," Proc. Nat'l Acad. Sci. (USA) 90(22):10841-10845, 1993.
Geschwind, M.D., et al., "Defective HSV-1 Vector Expressing BDNF in Auditory Ganglia Elicits Neurite Outgrowth: Model for Treatment of Neuron Loss Following Cochlear Degeneration," Human Gene Therapy 7:173-182, 1996.

(Continued)

Primary Examiner—Brian Whiteman
(74) Attorney, Agent, or Firm—Christensen O'Connor Johnson Kindness PLLC

(57) ABSTRACT

The present invention provides methods for stimulating the formation of inner ear cells, including inner ear sensory hair cells and inner ear support cells. The methods of the present invention damage and/or kill inner ear cells, and stimulate the formation of new, inner ear cells.

8 Claims, 6 Drawing Sheets

OTHER PUBLICATIONS

Guan K.-L., et al., "Growth Suppression by p18, and p16$^{INK4/MTS1}$- and p14$^{INK4B/MTS2}$-Related CDK6 Inhibitor, Correlates with Wild-Type pRb Function," *Genes Dev.* 8(24):2939-2952, 1994.

Hannon, G.J., and D. Beach, "p15$^{INK4B}$ is a Potential Effector of TGF-β-Induced Cell Cycle Arrest," *Nature* 371(6494):257-261, 1994.

Huang, M.-T., et al., "Inhibitory Effects of Curcumin on Tumorigenesis in Mice," *Journal of Cellular Biochemistry Supplement* 27:26-34, 1997 (ACS Abstract No. 129:62545).

Kil, J., et al., "Life, Death and Lipofection of the Cultured Mouse Organ of Corti From age of Hearing Onset," *ARO abs* 21:672, 1998.

Lalwani, A.K., et al., "Green Fluorescent Protein as a Reporter for Gene Transfer Studies in the Cochlea," *Hearing Research* 114:139-147, 1997.

LeBlanc, C.S., et al., "Phosphorothioate Oligodeoxynucleotides can Selectively Alter Neuronal Activity in the Cochlea," *Hear Res.* 135:105-112, 1999.

Lee, M.-H., et al., "Cloning of p57$^{KIP2}$, a Cyclin-Dependent Kinase Inhibitor with Unique Domain Structure and Tissue Distribution," *Genes Dev.* 9(6):639-649, 1995.

Liu, W., et al., "All Brn3 Genes can Promote Retinal Ganglion Cell Differentiation in the Chick," *Development Abstract*, 2002.

Löwenheim, H., et al., "Gene Distribution of p27$^{Kip1}$ allows Cell Proliferation in the Postnatal and Adult Organ of Corti," *Proc. Nat'l Acad. Sci. USA* 96:4084-4088, 1999.

McEvilly, R.J. and M.G. Rosenfeld, "The Role of POU Domain Proteins in the Regulation of Mammalian Pituitary and Nervous System Development," *Progress in Nucleic Acid Research and Molecular Biology* 64:223-255, 2000.

Nakai, Y., et al., "Ototoxicity of the Anticancer Drug Cisplatin," *Acta Otolaryngol* 93:227-232, 1982.

Parietti, C., et al., "Attempt at Hair Cell Neodifferentiation in Developing and Adult Amikacin Intoxicated Rat Cochleae," *Brain Research* 813(1):57-66, 1998.

Polyak, K., et al., "Cloning of p27$^{Kip1}$, A Cyclin-Dependent Kinase Inhibitor and a Potential Mediator of Extracellular Antimitogenic Signals," *Cell* 78(1):59-66, 1994.

Ryan, A.F., "Transcriptional Factors and the Control of Inner Ear Development." *Seminars in Cell & Developmental Biology* 8:249-256, 1997.

Serrano, M., et al., "A New Regulatory Motif in Cell-Cycle Control Causing Specific Inhibition of Cyclin D/CDK4," *Nature* 366(6456):704-707, 1993.

Shankland, S.J., et al., "Mesangial Cell Proliferation Mediated by PDGF and bFGF Is Determined by Levels of the Cyclin Kinase Inhibition p27(Kip1)," *Kidney Int.* 51(4):1088-1099, 1997 (EMBASE Abstract No. 97130705).

Shankland, S.J., et al., "Cyclin Kinase Inhibitors are Increased During Experimental Membranous Nephropathy: Potential Role in Limiting Glocerular Epithelial Cell Proliferation *In Vivo*," *Kidney International* 52(2):404-413, 1997.

Shulman, A., "The Cochleovestibular System/Ototoxicity/Clinical Issues," *Ann. NY Acad. Sci.* 884:433-436, 1999.

Simson, R., et al., "Evaluating the In Vivo Elastic Properties of Different Strands of Dictyostelium Discoideum Using Small Shear Forces," Technische Universität, München, Germany Abstract (BIOSIS Abstract No. 1997:441346).

Stöver, T., et al., "Cochlear Gene Transfer: Round Window Versus Cochleostomy Inoculation," *Hearing Research* 136:124-130, 1999.

Vahava, O., et al. "Mutation in Transcription Factor *POU4F3* Associated With Inherited Progressive Hearing Loss in Humans," *Science* 279(5358):1950-1954, 1998.

Verma, I.M., and N. Somia, "Gene Therapy—Promises, Problems and Prospects," *Nature* 389:239-242, 1997.

Waters, C., "Molecular Mechanisms of Cell Death in the Ear," *Ann NY Acad. Sci.* 884:41-51, 1999.

Xiang, M., et al., "*Brn-3b*: A POU Domain Gene Expressed in a Subset of Retinal Ganglion Cells," *Neuron* 11:689-701, 1993.

Xiang, M., et al., "Essential Role of POU-Domain Factor Brn-3c in Auditory and Vestibular Hair Cell Development," *Proc. Nat'l Acad. Sci. (USA)* 94(17):9445-9450, 1997.

Xiang, M., et al., "The Brn-3 Family of POU-Domain Factors: Primary Structure, Binding Specificity, and Expression in Subsets of Retinal Ganglion Cells and Somatosensory Neurons," *J. Neurosci.* 157(7 Part 1):4762-4785, 1995.

\* cited by examiner

STIMULATION OF CELLULAR REGENERATION AND DIFFERENTIATION IN THE INNER EAR

CROSS-REFERENCE TO RELATED APPLICATIONS

This application is a continuation of prior application Ser. No. 09/614,099, filed July 11, 2000, now abandoned, which is a continuation-in-part of International Application No. PCT/US00/05736, filed Mar. 3, 2000, and International Application No. PCT/EP99/01153, filed Feb. 23, 1999.

FIELD OF THE INVENTION

The present invention relates to methods and compositions for stimulating the formation of inner ear cells, including inner ear sensory hair cells and inner ear support cells.

BACKGROUND OF THE INVENTION

Sensorineuronal hearing loss (SNHL), also called "nerve deafness," is a significant communication problem that affects tens of millions of people in the U.S. alone. Loss of the inner ear sensory hair cells that detect sound is thought to be a major cause of this deficit. The anatomy of the inner ear is well known to those of ordinary skill in the art (see, e.g., *Gray's Anatomy*, Revised American Edition (1977), pages 859–867, incorporated herein by reference). In brief, the inner ear includes three sensory portions: the cochlea, which senses sound; the semicircular canals, which sense angular acceleration; and the otolithic organs, which sense linear acceleration. In each of these sensory portions, specialized sensory hair cells are arrayed upon one or more layers of inner ear supporting cells. Supporting cells underlie, at least partially surround, and physically support sensory hair cells within the inner ear. In operation, the sensory hair cells are physically deflected in response to sound or motion, and their deflection is transmitted to nerves which send nerve impulses to the brain for processing and interpretation.

In mammals, the inner ear is normally incapable of regenerating damaged or dead inner ear sensory hair cells. Thus, hearing disorders that result from the death or deterioration of sensory hair cells typically result in a permanent hearing impairment. Sensorineuronal hearing loss can be caused by a multitude of events including age-related loss (presbycusis), noise exposure, drug exposure (e.g., antibiotics and anti-cancer therapeutics), infections, genetic mutations (syndromic and non-syndromic) and autoimmune disease.

Currently, the treatment for acquired sensorineuronal hearing loss involves the use of external hearing aids and cochlear implants. Both devices have rather limited therapeutic potential and more importantly, do not address the problem of restoring structure or function to the auditory sensory epithelium.

A more recent approach to the problem of regenerating sensory inner ear hair cells is disclosed in published international application serial number PCT/US99/24829 which discloses methods for stimulating the regeneration of inner ear cells (including sensory hair cells) that include the step of introducing into inner ear cells nucleic acid molecules that encode a transcription factor capable of stimulating the regeneration of inner ear cells.

The present inventors have discovered that destruction of existing inner ear sensory hair cells promotes the re-entry of normally quiescent inner ear supporting cells (that express reduced levels of one or more cell cycle inhibitor proteins, or in which cell cycle protein activity has been reduced) into the cell cycle to yield progeny cells that can be induced to form inner ear sensory hair cells, as disclosed herein. In some instances, destruction of existing inner ear sensory hair cells is sufficient to stimulate underlying and/or surrounding inner ear support cells to develop into sensory hair cells. In other instances, efficient regeneration of sensory hair cells from support cells requires destruction of existing inner ear sensory hair cells in combination with at least one other stimulus, as described herein. Additionally, the present inventors have discovered that stimulating the proliferation of inner ear support cells (with or without stimulating the regeneration of inner ear sensory hair cells) improves the auditory function of the inner ear.

SUMMARY OF THE INVENTION

The present invention provides methods for stimulating the formation of inner ear cells, including inner ear sensory hair cells and inner ear support cells. The methods of the present invention rely on the unexpected observation that damaging and/or killing inner ear cells stimulates the formation of new, inner ear cells.

In one aspect, the present invention provides methods for stimulating the formation of inner ear sensory hair cells from inner ear support cells. The methods of this aspect of the present invention include the step (a) of damaging one or more inner ear sensory hair cells under conditions that promote the formation of one or more new sensory hair cells from one or more support cells that are in contact with the damaged sensory hair cell(s). Preferably a plurality of inner ear sensory hair cells are formed from a plurality of inner ear support cells. The methods of this aspect of the invention optionally include the step (b) of further stimulating the formation of one or more inner ear sensory hair cells from inner ear support cells that are in contact with the damaged inner ear sensory hair cell. Step (b) can occur before, during, after or overlapping with step (a). In one embodiment, the step of stimulating the formation of one or more inner ear sensory hair cells from one or more inner ear support cells that are in contact with the damaged inner ear sensory hair cell includes the steps of stimulating the inner ear support cells to enter the cell cycle, then stimulating at least some of the progeny of the inner ear support cells to differentiate to form inner ear sensory hair cells.

Inner ear sensory hair cells can be damaged, for example, by contact with an amount of an ototoxic agent, such as an antibiotic, preferably an aminoglycoside antibiotic, that is effective to damage inner ear sensory hair cells. The ototoxic agent can be introduced into the inner ear by any art-recognized means, for example by injection (such as with a needle and syringe), or through a cannula. In one embodiment of this aspect of the invention, inner ear sensory hair cells are sufficiently damaged to cause their death.

In some embodiments of the present invention, damage inflicted on an inner ear sensory hair cell stimulates the formation of one or more new inner ear sensory hair cell from an inner ear support cell that is in contact with the damaged inner ear sensory hair cell. In other embodiments, however, damage inflicted on an inner ear sensory hair cell is insufficient, by itself, to efficiently stimulate the formation of one or more new inner ear sensory hair cells from an inner ear support cell that is in contact with the damaged inner ear sensory hair cell. Thus, in one embodiment of the methods of this aspect of the present invention, the formation of inner ear sensory hair cells from inner ear support cells is stimulated by damaging inner ear sensory hair cells and expressing within inner ear support cells (before, during and/or after the step of damaging sensory hair cells) a transcription factor capable of stimulating inner ear sensory hair cells to form from inner ear support cells. For example, in one embodiment of the present invention, a nucleic acid molecule encoding a transcription factor capable of stimulating inner ear sensory hair cells to form from inner ear support cells is introduced into inner ear support cells under conditions that enable expression of the transcription factor. Representative examples of transcription factors capable of stimulating the formation of inner ear sensory hair cells from inner ear support cells include POU4F1, POU4F2, POU4F3, Brn3a, Brn3b and Brn3c.

In another embodiment of the methods of this aspect of the present invention, the formation of inner ear sensory hair cells from inner ear support cells is stimulated by damaging inner ear sensory hair cells and inhibiting (before, during and/or after the step of damaging the sensory hair cells) the expression of one or more cell cycle inhibitors active in inner ear support cells. Inhibitors of cell cycle inhibitors can be substances, such as proteins, that act on the cell cycle inhibitor directly or indirectly within the cell. By way of representative example, cell cycle inhibitors active in inner ear support cells include cyclin-dependent kinase inhibitors, such as cyclin-dependent kinase inhibitors of the so-called CIP/KIP family including $p21^{Cip1}$, $p27^{Kip1}$ and $p57^{Kip2}$. For example, the expression of a cell cycle inhibitor active in inner ear support cells can be inhibited by introducing into inner ear support cells an expression vector that expresses a nucleic acid molecule that hybridizes under stringent conditions (such as stringency greater than 2×SSC at 55° C.) to a nucleic acid molecule (such as an mRNA molecule) encoding a cell cycle inhibitor active in inner ear support cells.

In addition, various recombinant growth factors such as TGF-alpha, insulin and IGF-1 can be used to stimulate the formation of inner ear sensory hair cells from inner ear support cells. A representative, effective concentration range for recombinant growth factors utilized in vitro in the practice of the present invention is 1–1000ng/ml. More specifically, TGF-alpha is preferably used at an effective concentration of from 1–100 ng/ml; insulin is preferably used at an effective concentration of from 100–1000 ng/ml; and IGF-1 is preferably used at an effective concentration of from 10–1000 ng/ml. For in vivo applications, a sufficient amount of recombinant growth factor would be administered to produce the foregoing concentrations in vivo.

In preferred embodiments of this aspect of the invention, the formation of inner ear sensory hair cells from inner ear support cells results in improvement in the auditory function of the treated inner ear. Thus, in one aspect, the invention provides methods for improving auditory function in an inner ear comprising the steps of: (a) damaging a first inner ear sensory hair cell under conditions that promote the formation of one or more new inner ear sensory hair cells from a support cell that is in contact with the damaged, first inner ear sensory hair cell; and (b) measuring an improvement in auditory function in the inner ear treated in accordance with step (a).

In another aspect, the present invention provides methods for stimulating the formation of inner ear support cells. The methods of this aspect of the invention include the steps of damaging inner ear support cells under conditions that promote the formation of new inner ear support cells (for example by cell division of inner ear support cells that are in contact with damaged inner ear support cells). In this aspect of the invention, the inner ear support cell is damaged, and the formation of new inner ear support cells is stimulated, using the same techniques described herein for the methods of the present invention that stimulate the formation of inner ear sensory hair cells from inner ear support cells. Thus, for example, inner ear support cells can be damaged by contact with an amount of an ototoxic agent, such as an aminoglycoside antibiotic, that is effective to damage inner ear support cells. Again by way of example, new inner ear support cell formation can be further stimulated by damaging inner ear support cells and expressing (before, during and/or after damaging inner ear support cells) within inner ear support cells a transcription factor (such as POU4F1, POU4F2, POU4F3, Brn3a, Brn3b and Brn3c) capable of stimulating inner ear support cells to divide and form new inner ear support cells. In preferred embodiments of this aspect of the invention, the proliferation of inner ear support cells results in improvement in the auditory function of the treated inner ear.

The methods of the present invention are useful for stimulating the formation of inner ear cells, such as sensory hair cells and support cells. Further, the methods of the present invention are useful to ameliorate the symptoms of a hearing disorder in a mammal, such as a human, that is caused by the death or damage of inner ear cells. Additionally, the methods of the present invention can be used to identify genes and/or proteins that are capable of stimulating the formation of inner ear support cells and/or the formation of inner ear sensory hair cells from inner ear support cells.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
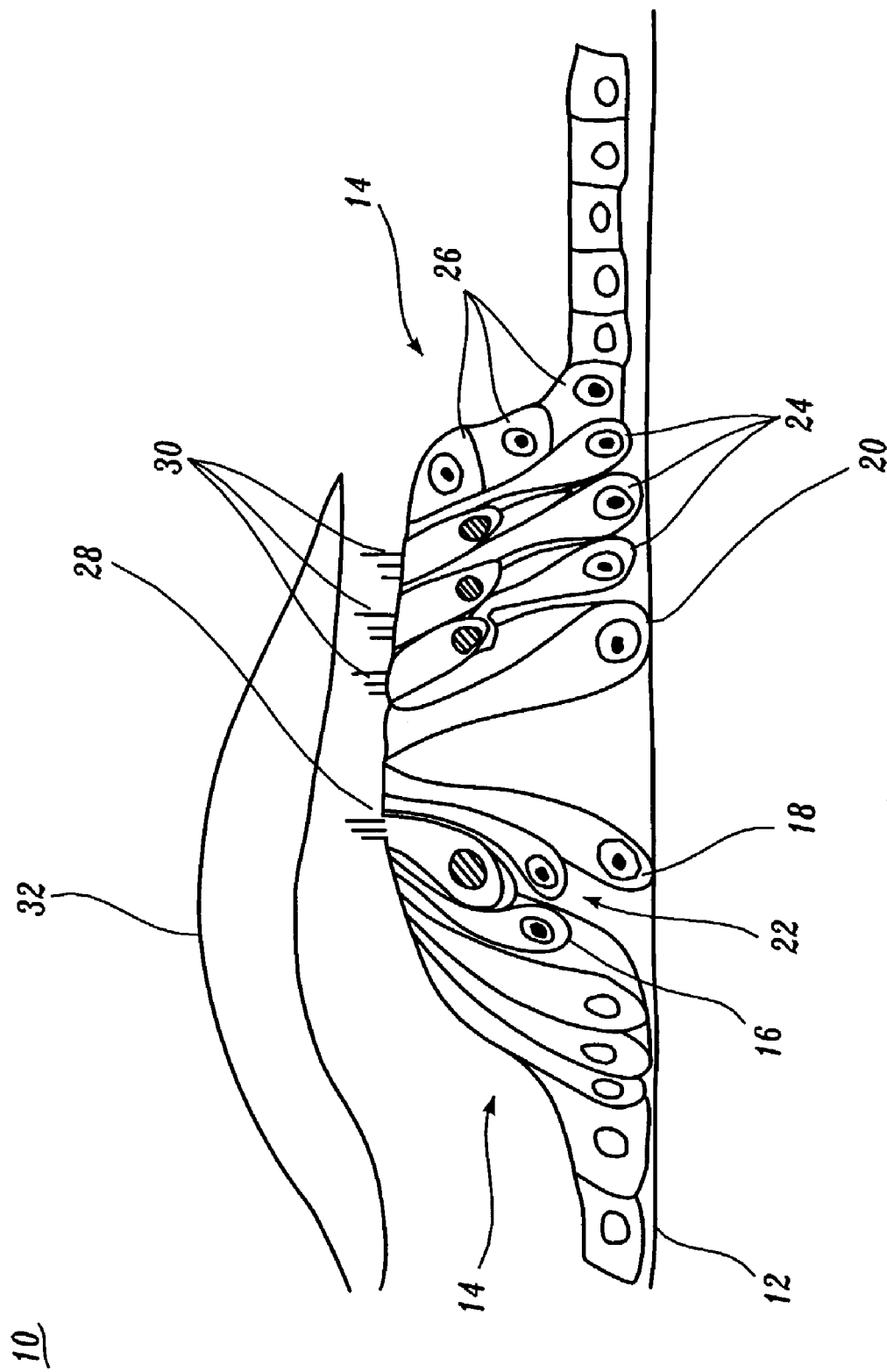
FIG. 1 shows a cross section of the Organ of Corti.
Figure 2:
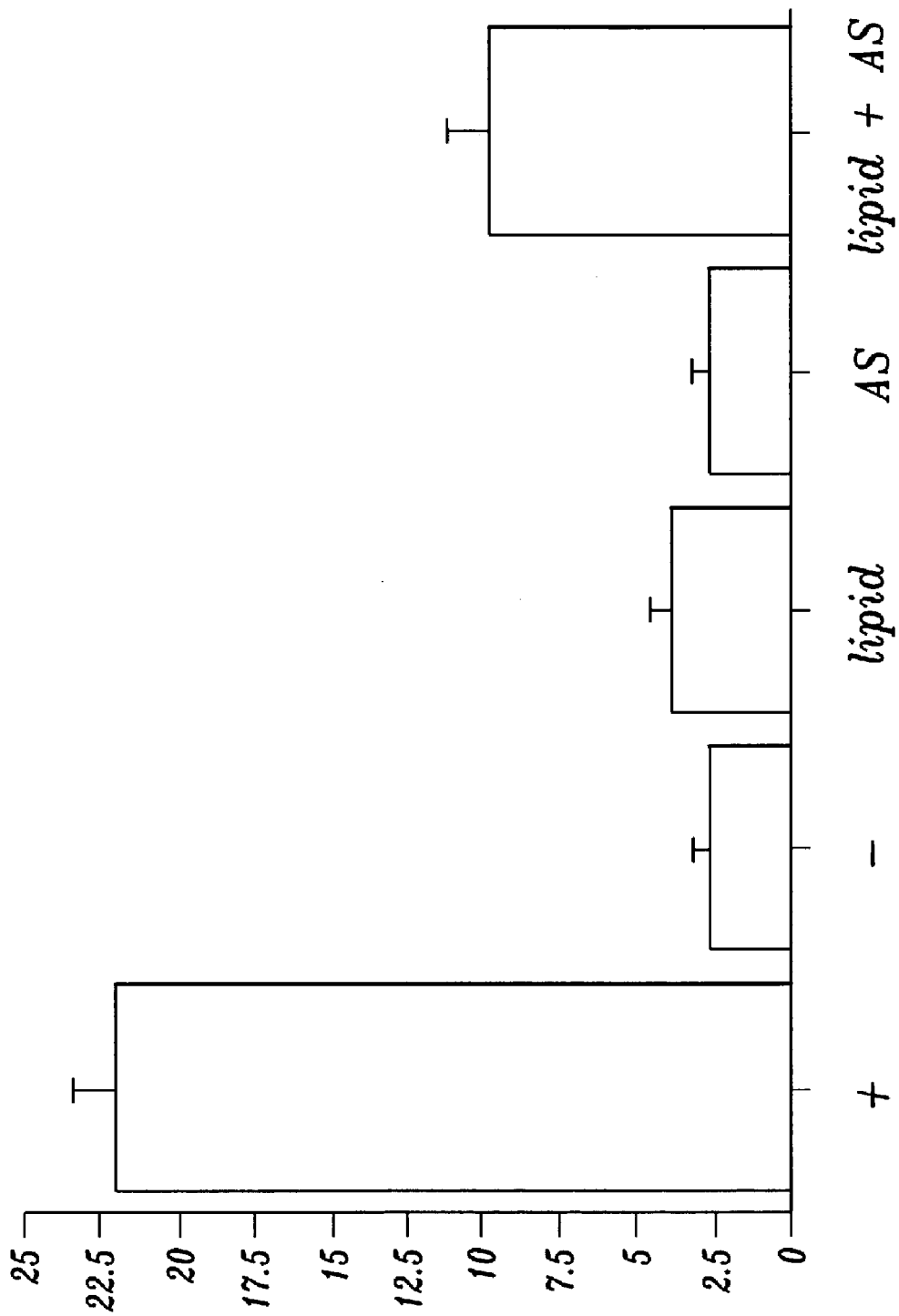
FIG. 2 shows the number of BrdU-labeled, guinea pig JH4 cells following serum deprivation for 24 hours and a BrdU pulse for the last 4 hours of the 24 hour period. Cells were counted under fluorescence microscopy. The combination of lipids and $p27^{kip1}$ AS reversed growth arrest to 40% of that seen with 10% FBS stimulation (p<0.0001). (+) FBS; (−) no FBS; (AS) antisense oligonucleotide; (lipid) lipofection.
Figure 3:
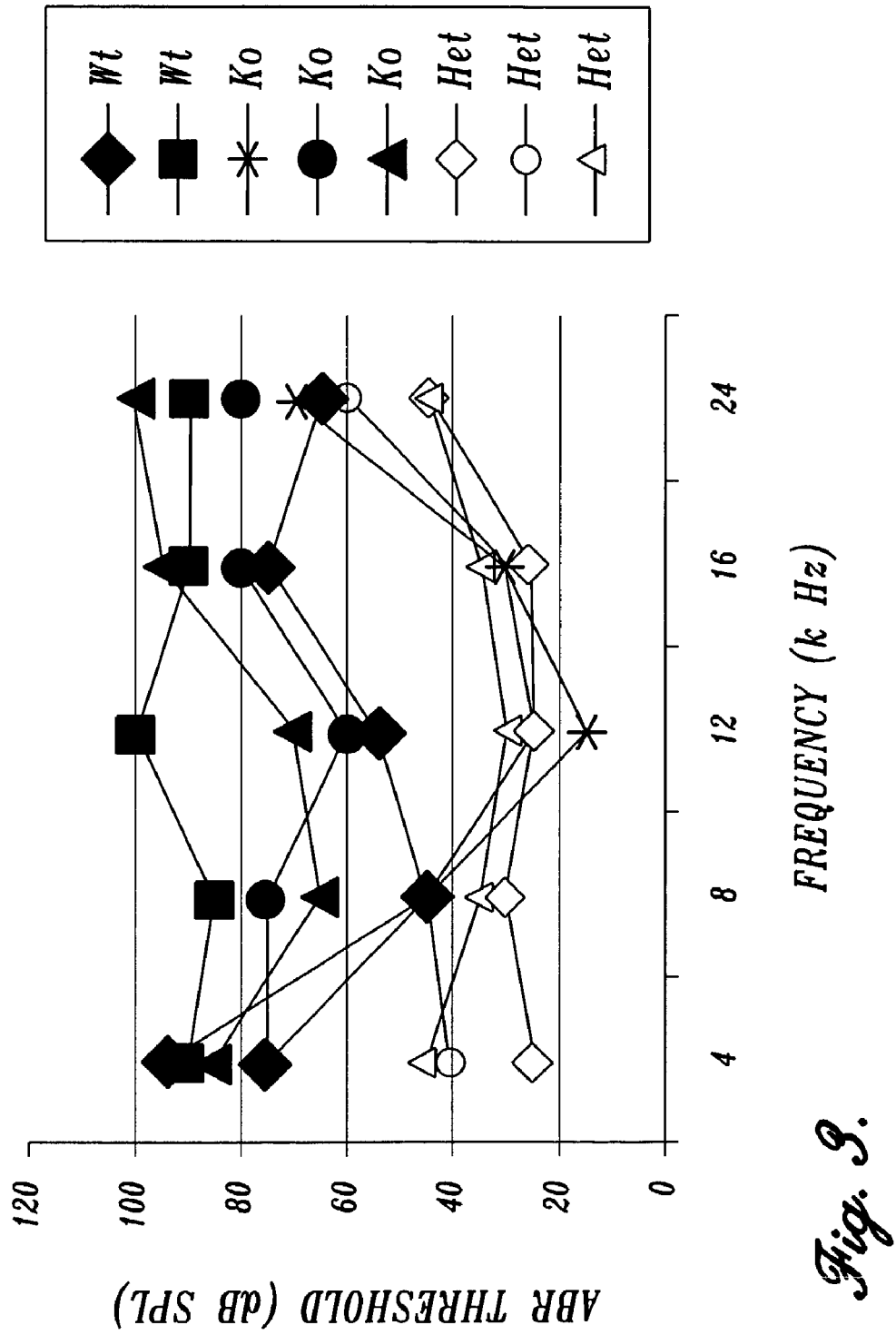
FIG. 3 shows the ABR threshold of the right ears of mice two weeks after the inner ears of the mice had been treated with amikacin sulfate. Abbreviations are: ABR, auditory brainstem response; dB, decibels; SPL, sound pressure level; Wt, wild type; Het, p27 heterozygote; Ko, p27 knock-out; kHZ, kilo Hertz.
Figure 4:
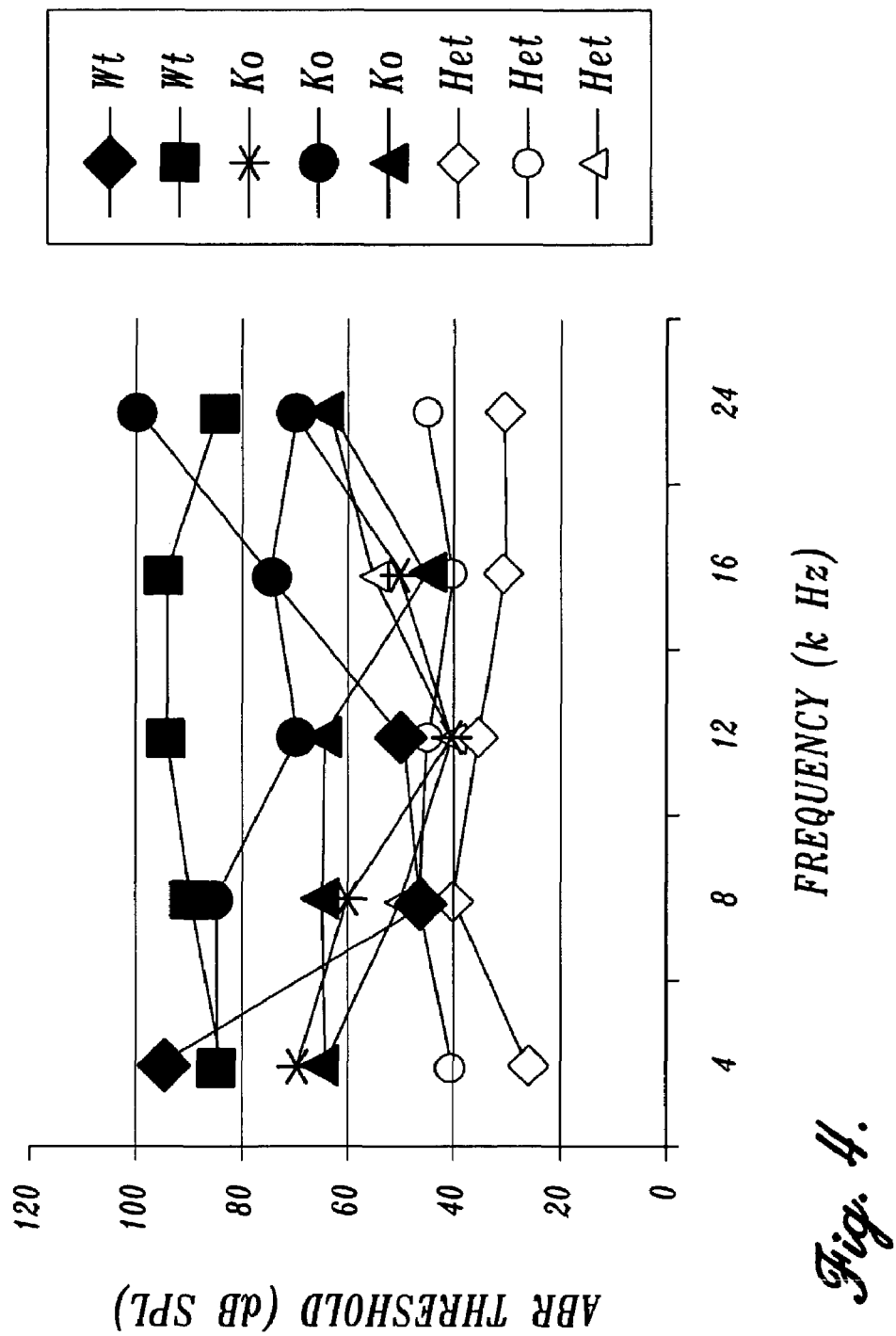
FIG. 4 shows the ABR threshold of the left ears of mice two weeks after the inner ears of the mice had been treated with amikacin sulfate. Abbreviations are the same as those set forth in the description of FIG. 3.
Figure 5:
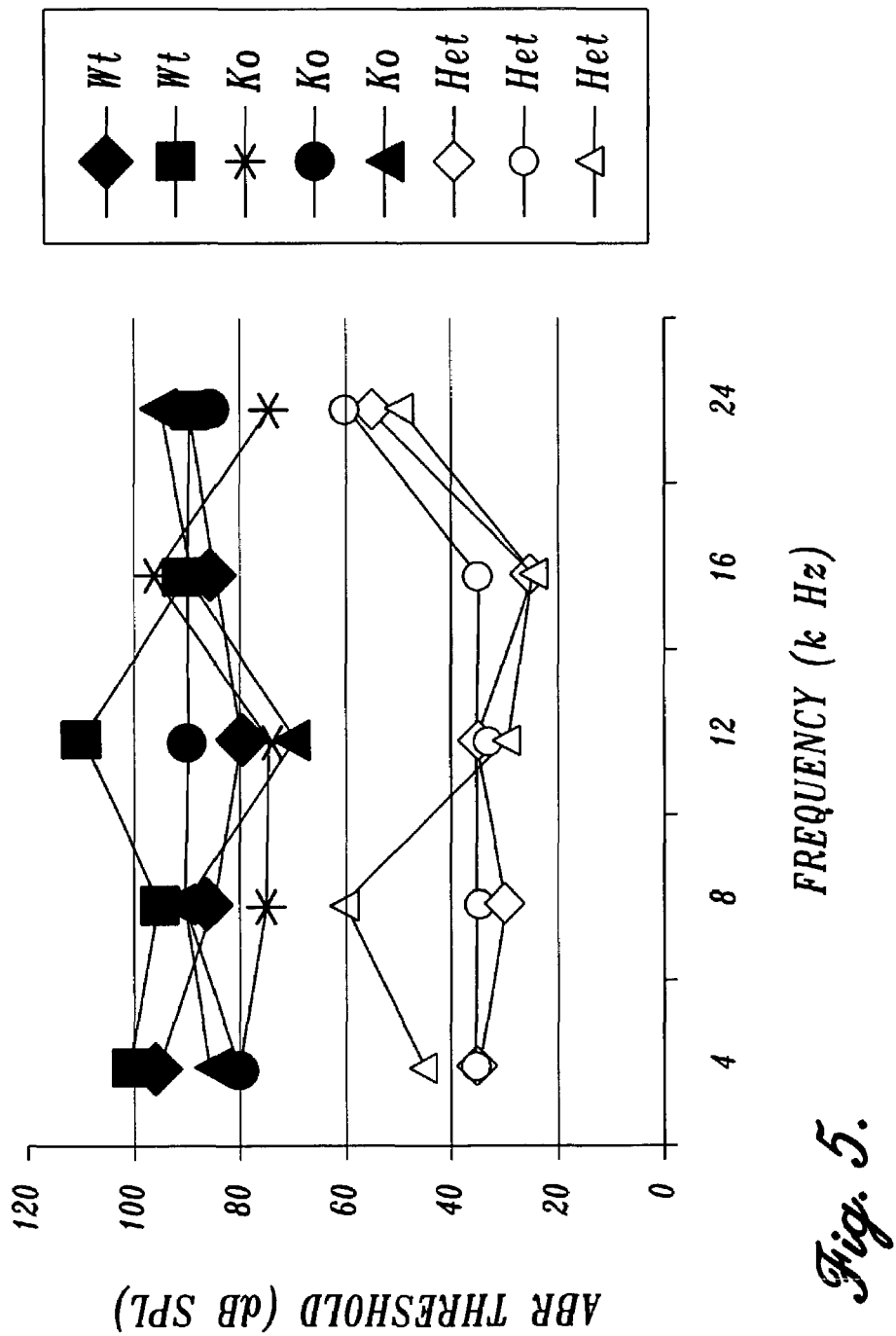
FIG. 5 shows the ABR threshold of the right ears of mice four weeks after the inner ears of the mice had been treated with amikacin sulfate. Abbreviations are the same as for FIG. 3.
Figure 6:
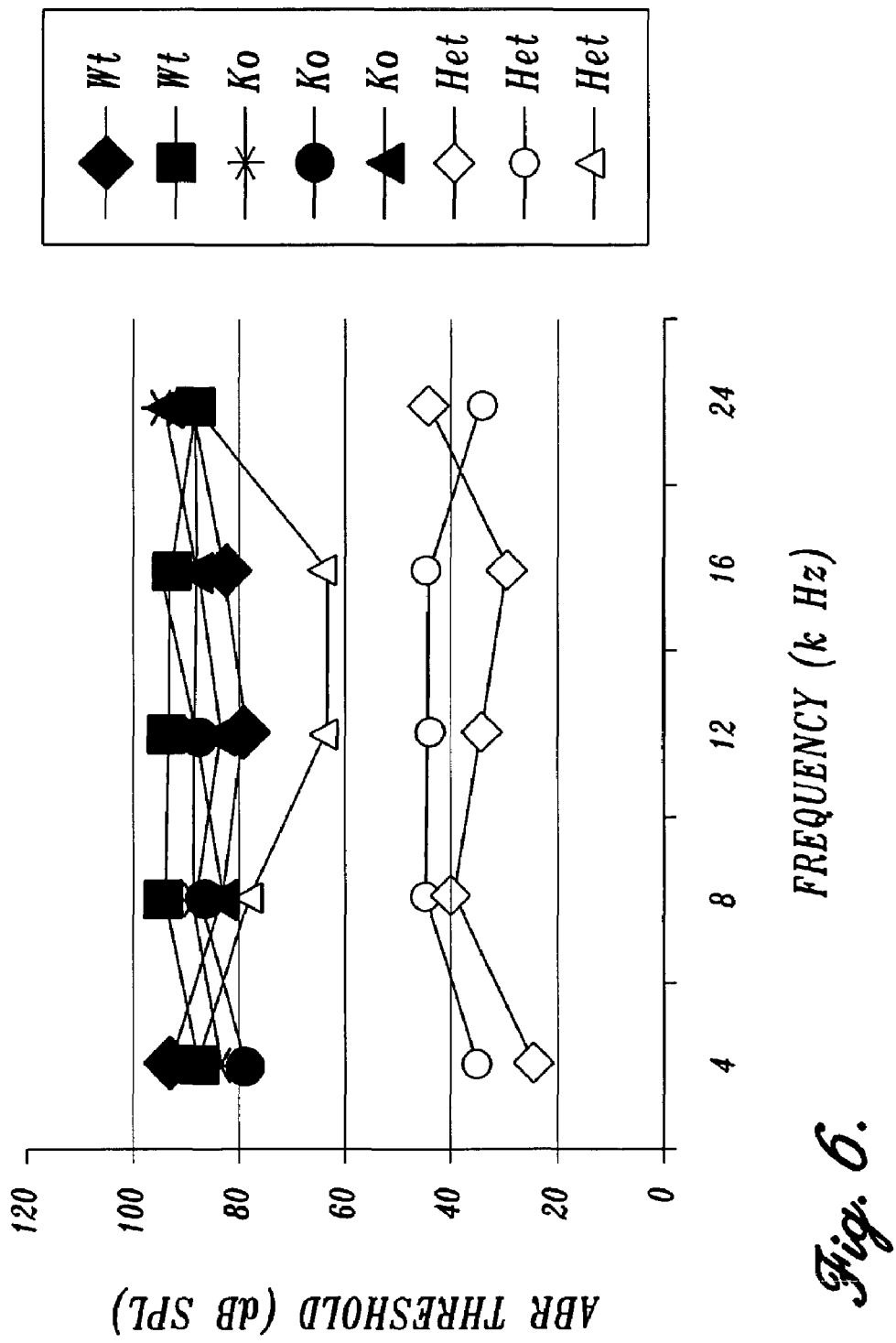
FIG. 6 shows the ABR threshold of the left ears of mice four weeks after the inner ears of the mice had been treated with amikacin sulfate. Abbreviations are the same as for FIG. 3.

As used herein, the abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

As used herein, the phrase "damaging one or more inner ear sensory hair cells", or "damaging a first inner ear sensory hair cell", or grammatical equivalents thereof, means causing a deleterious change in the structure, biochemistry and/or physiology of the damaged, sensory hair cell (including killing the damaged cell) compared to an inner ear sensory hair cell that is cultured under substantially the same conditions as the damaged cell, but which is not damaged.

As used herein, the phrase "improving auditory function" or "improvement in auditory function", or grammatical equivalents thereof, means improving, by at least 10%, the sensitivity to sound of an inner ear by treating the inner ear in accordance with the methods of the present invention, or effecting any measurable improvement in the sensitivity to sound of an inner ear that is completely unresponsive to sound prior to treatment in accordance with the present invention. The sensitivity to sound of the treated inner ear is measured by any art-recognized means (such as the auditory brainstem response) and compared to the sensitivity to sound of a control inner ear that is not treated in accordance with the present invention and which is cultured under substantially the same conditions as the treated inner ear.

As applied to nucleic acid sequence comparisons or amino acid sequence comparisons herein, the term "sequence homology" (also referred to as "sequence identity") is defined as the percentage of amino acid residues or nucleic acid residues in a subject amino acid sequence or nucleic acid sequence that are identical with part or all of a candidate amino acid sequence or nucleic acid sequence, after aligning the sequences and introducing gaps, if necessary, to achieve the maximum percent homology (identity), and not considering any conservative substitutions as part of the sequence homology. Neither N- or C-terminal extensions nor insertions shall be construed as reducing homology. No weight is given to the number or length of gaps introduced, if necessary, to achieve the maximum percent homology (identity).

In one aspect, the present invention provides methods for stimulating the formation of inner ear sensory hair cells from inner ear support cells. The methods of this aspect of the present invention include the step (a) of damaging one or more inner ear sensory hair cells under conditions that promote the formation of one or more new sensory hair cells from one or more support cells that are in contact with the damaged sensory hair cell(s). Preferably a plurality of inner ear sensory hair cells are formed from a plurality of inner ear support cells. The methods of this aspect of the invention optionally include the step (b) of further stimulating the formation of one or more inner ear sensory hair cells from inner ear support cells that are in contact with the damaged inner ear sensory hair cell. Step (b) can occur before, during, after or overlapping with step (a). The methods of this aspect of the present invention can be utilized in vivo and in vitro.

The anatomy of the inner ear is well known to those of ordinary skill in the art (see, e.g., *Gray's Anatomy*, Revised American Edition (1977), pages 859–867, incorporated herein by reference). In particular, the cochlea includes the Organ of Corti which is primarily responsible for sensing sound. As shown in FIG. 1, the Organ of Corti 10 includes a basilar membrane 12 upon which are located a variety of supporting cells 14, including border cells 16, inner pillar cells 18, outer pillar cells 20, inner phalangeal cells 22, Dieter's cells 24 and Hensen's cells 26. Supporting cells 14 support inner hair cells 28 and outer hair cells 30. Tectorial membrane 32 is disposed above inner hair cells 28 and outer hair cells 30. The present invention is adapted, in one aspect, to stimulate regeneration of sensory hair cells 28 and 30 from underlying supporting cells 14. In another aspect, the present invention is adapted to stimulate the formation of supporting cells 14.

The present inventors have observed that destruction of existing inner ear sensory hair cells promotes the re-entry of normally quiescent inner ear supporting cells into the cell cycle to yield progeny cells that can be induced to form inner ear sensory hair cells as disclosed herein. In some instances, destruction of existing inner ear sensory hair cells is sufficient to stimulate underlying and/or surrounding inner ear support cells to develop into sensory hair cells. In other instances, efficient regeneration of sensory hair cells from support cells requires destruction of existing inner ear sensory hair cells in combination with another stimulus, as described herein.

In the practice of one aspect of the present invention, inner ear sensory hair cells are damaged, for example by contact with an amount of an ototoxic agent that is effective to damage inner ear sensory hair cells. Representative examples of ototoxic agents useful for damaging inner ear sensory hair cells include aminoglycoside antibiotics (such as, neomycin, gentamycin, streptomycin, kanamycin, amikacin and tobramycin). In the practice of the present invention, the foregoing aminoglycoside antibiotics are typically used in vitro at an effective concentration in the range of from about 0.01 mM–10 mM, and in vivo at an effective concentration in the range of from about 100 to about 1,000 milligrams per kilogram body weight per day (mg/kg/d). Additional, representative examples of chemical agents useful for damaging inner ear sensory hair cells include the following anti-cancer agents: cisplatin, carboplatin and methotrexate which are typically used in vitro at an effective concentration in the range of from about 0.01–0.1 mM, and in vivo at an effective concentration in the range of from about 5 to about 10 mg/kg/d. Other useful chemical agents include poly-L-lysine at an effective concentration in the range of from about 0.1–1.0 mM in vitro, and magnesium chloride at an effective concentration in vitro in the range of from about 5–100 mM.

The ototoxic agent, or agents, can be introduced into the inner ear by any art-recognized means, for example by injection using a needle and syringe, or by cochleostomy. Cochleostomy involves puncturing the cochlea and inserting a catheter through which a chemical agent can be introduced into the cochlea. A cochleostomy method is disclosed, for example, in Lalwani, A. K. et al., *Hearing Research* 114: 139–147 (1997), which publication is incorporated herein by reference.

In one embodiment of the methods of the present invention, the formation of inner ear sensory hair cells from inner ear support cells is stimulated by damaging inner ear sensory hair cells and expressing (before, during, and/or after damaging the inner ear sensory hair cells) within at least some of the inner ear support cells a transcription factor capable of stimulating the formation of an inner ear sensory hair cell from an inner ear support cell. For example, in one embodiment, a nucleic acid molecule encoding a transcription factor capable of stimulating the formation of an inner ear sensory hair cell is introduced into inner ear support cells under conditions that enable expression of the transcription factor.

Transcription factors useful in this aspect of the present invention have the ability to stimulate regeneration of inner ear sensory hair cells from inner ear supporting cells when utilized in the practice of the methods of the present invention. Some transcription factors useful in this aspect of the present invention are required for the normal development, and/or for the normal functioning, of inner ear sensory hair cells.

Representative examples of transcription factors useful in this aspect of the present invention include POU4F1 (Collum, R. G. et al., *Nucleic Acids Research* 20(18):4919–4925 (1992)), POU4F2 (Xiang et al., *Neuron* 11:689–701 (1993)), POU4F3 (Vahava, O., *Science* 279(5358):1950–1954 (1998), Brn3a (also known as Brn3.0), Brn3b (also known as Brn3.2) and Brn3c (also known as Brn3.1) as disclosed in Gerrero et al., *Proc. Nat'l. Acad. Sci.* (U.S.A.) 90(22): 10841–10845 (1993), Xiang, M. et al., *Proc. Nat'l. Acad. Sci.* (U.S.A.) 93(21):11950–11955 (1996), Xiang, M. et al., *J. Neurosci.* 15(7Part 1):4762–4785 (1995), Erkman, L. et al., *Nature* 381(6583):603–606 (1996), Xiang, M. et al., *Proc. Nat'l. Acad. Sci.* (U.S.A.) 94(17): 9445–9450 (1997), each of which publications is incorporated herein by reference. Some transcription factors useful in this aspect of the present invention possess at least one homeodomain and/or at least one POU-specific domain, and have a molecular weight in the range of from about 33 kDa to about 37 kDa.

As used herein, the term "homeodomain" means an amino acid sequence that is at least 50% homologous (such as at least 75% homologous, or at least 90% homologous) to the homeodomain amino acid sequence set forth in SEQ ID NO:1.

As used herein, the term "POU-specific domain" means an amino acid sequence that is at least 50% homologous (such as at least 75% homologous, or at least 90% homologous) to the POU-specific domain amino acid sequence set forth in SEQ ID NO:2.

An example of an algorithm that can be used to determine the percentage homology between two protein sequences, or between two nucleic acid sequences, is the algorithm of Karlin and Altschul (*Proc. Natl. Acad. Sci. USA* 87:2264–2268 (1990)), modified as in Karlin and Altschul (*Proc. Natl. Acad. Sci. USA* 90:5873–5877 (1993)). Such an algorithm is incorporated into the NBLEST and XBLEST programs of Altschul et al. (*J. Mol. Biol.* 215:403–410 (1990)).

Presently more preferred inner ear cell transcription factors useful in the practice of the present invention are POU4F3 transcription factor homologues (hereinafter referred to as POU4F3 homologues). POU4F3 homologues useful in the practice of the present invention are capable of stimulating the regeneration of inner ear sensory hair cells from supporting cells and are at least 25% homologous (such as at least 50% homologous or at least 75% homologous, or at least 90% homologous) to the POU4F3 transcription factor having the amino acid sequence set forth in SEQ ID NO:4 and which is encoded by the nucleic acid molecule of SEQ ID NO:3. As used herein, the term "POU4F3 homologues" includes the POU4F3 protein having the amino acid sequence set forth in SEQ ID NO:4, which is the presently most preferred inner ear cell transcription factor useful in the practice of the present invention. Representative examples of other POU4F3 homologues useful in the practice of the present invention are set forth in Xiang, M. et al., *J. Neuroscience* 15(7):4762–4785 (1995), which publication is incorporated herein by reference.

Additional nucleic acid molecules encoding transcription factors useful in the practice of the present invention can be isolated by using a variety of cloning techniques known to those of ordinary skill in the art. For example, cloned POU4F3 homologues cDNAs or genes, or fragments thereof, can be used as hybridization probes utilizing, for example, the technique of hybridizing radiolabeled nucleic acid probes to nucleic acids immobilized on nitrocellulose filters or nylon membranes as set forth at pages 9.52 to 9.55 of *Molecular Cloning, A Laboratory Manual* (2nd edition), J. Sambrook, E. F. Fritsch and T. Maniatis eds., the cited pages of which are incorporated herein by reference. Presently preferred hybridization probes for identifying additional nucleic acid molecules encoding POU4F3 homologues are fragments, of at least 15 nucleotides in length, of the cDNA molecule (or its complementary sequence) having the nucleic acid sequence set forth in SEQ ID NO:3, although the complete cDNA molecule having the nucleic acid sequence set forth in SEQ ID NO:3 is also useful as a hybridization probe for identifying additional nucleic acid molecules encoding POU4F3 homologue. A presently most preferred hybridization probe for identifying additional nucleic acid molecules encoding POU4F3 homologues is the oligonucleotide having the nucleic acid sequence 5'-TAG AAG TGC AGG GCA CGC TGC TCA TGG TAT G-3' (SEQ ID NO:5).

Exemplary high stringency hybridization and wash conditions useful for identifying (by Southern blotting) additional nucleic acid molecules encoding POU4F3 homologues are: hybridization at 68° C. in 0.25 M $Na_2HPO_4$ buffer (pH 7.2) containing 1 mM $Na_2EDTA$, 20% sodium dodecyl sulfate; washing (three washes of twenty minutes each at 65° C.) is conducted in 20 mM $Na_2HPO_4$ buffer (pH 7.2) containing 1 mM $Na_2EDTA$, 1% (w/v) sodium dodecyl sulfate.

Exemplary moderate stringency hybridization and wash conditions useful for identifying (by Southern blotting) additional nucleic acid molecules encoding POU4F3 homologues are: hybridization at 45° C. in 0.25 M $Na_2HPO_4$ buffer (pH 7.2) containing 1 mM $Na_2EDTA$, 20% sodium dodecyl sulfate; washing is conducted in 5×SSC, containing 0.1% (w/v) sodium dodecyl sulfate, at 55° C. to 65° C.

Again, by way of example, nucleic acid molecules encoding transcription factors useful in the present invention can be isolated by the polymerase chain reaction (PCR) described in *The Polymerase Chain Reaction* (K. B. Mullis, F. Ferre, R. A. Gibbs, eds), Birkhauser Boston (1994), incorporated herein by reference. Thus, for example, first strand DNA synthesis can be primed using an oligo (dT) primer, and second strand cDNA synthesis can be primed using an oligonucleotide primer that corresponds to a portion of the 5'-untranslated region of a cDNA molecule that is homologous to the target DNA molecule. Subsequent rounds of PCR can be primed using the second strand cDNA synthesis primer and a primer that corresponds to a portion of the 3'-untranslated region of a cDNA molecule that is homologous to the target DNA molecule.

By way of non-limiting example, representative PCR reaction conditions for amplifying nucleic acid molecules encoding transcription factors useful in the present invention are as follows. The following reagents are mixed in a tube (on ice) to form the PCR reaction mixture: DNA template (e.g., up to 1 μg genomic DNA, or up to 0.1 μg cDNA), 0.1–0.3 mM dNTPs, 10 μl 10×PCR buffer (10×PCR buffer contains 500 mM KCl, 15 mM $MgCl_2$, 100 mM Tris-HCl, pH 8.3), 50 pmol of each PCR primer (PCR primers should preferably be greater than 20 bp in length and have a degeneracy of $10^2$ to $10^3$), 2.5 units of Taq DNA polymerase (Perkin Elmer, Norwalk, Conn.) and deionized water to a final volume of 50 µl. The tube containing the reaction mixture is placed in a thermocycler and a thermocycler program is run as follows. Denaturation at 94° C. for 2 minutes, then 30 cycles of: 94° C. for 30 seconds, 47° C. to 55° C. for 30 seconds, and 72° C. for 30 seconds to two and a half minutes.

Preferably, PCR primers will be designed against conserved amino acid sequence motifs found in some or all of the known target protein sequences. Examples of conserved amino acid sequence motifs against which PCR primers can be designed for cloning additional POU4F3 homologues are the POU-specific domain having the amino acid sequence set forth in SEQ ID NO:2, and the homeodomain having the amino acid sequence set forth in SEQ ID NO:1.

Further, additional nucleic acid molecules encoding transcription factors useful in the practice of the present invention can also be isolated, for example, by utilizing antibodies that recognize transcription factor proteins. Methods for preparing monoclonal and polyclonal antibodies are well known to those of ordinary skill in the art and are set forth, for example, in chapters five and six of *Antibodies A Laboratory Manual*, E. Harlow and D. Lane, Cold Spring Harbor Laboratory (1988), the cited chapters of which are incorporated herein by reference. By way of non-limiting example, antibodies were successfully raised against a fusion protein constructed from the C-terminal end of Brn3 as described in Xiang, M. et al., *J. Neuroscience* 15(7): 4762–4785 (1995) and Xiang, M. et al., *P.N.A.S.* (U.S.A.) 94:9445–9450 (1997), which publication is incorporated herein by reference.

Nucleic acid molecules that encode transcription factors useful in the practice of the present invention can be isolated, for example, by screening expression libraries. By way of non-limiting example, a cDNA expression library can be screened using anti-POU4F3 homologue antibodies in order to identify one or more clones that encode a POU4F3 homologue protein. DNA expression library technology is well known to those of ordinary skill in the art. Screening cDNA expression libraries is fully discussed in Chapter 12 of Sambrook, J., Fritsch, E. F. and Maniatis, T. (1989) *Molecular Cloning: A Laboratory Manual*, 2nd ed., Cold Spring Harbor Laboratory, Cold Spring Harbor, N.Y., the cited chapter of which is incorporated herein by reference.

By way of representative example, antigen useful for raising antibodies for screening expression libraries can be prepared in the following manner. A full-length cDNA molecule encoding a transcription factor, such as a POU4F3 homologue, (or a cDNA molecule that is not full-length, but which includes all of the coding region) can be cloned into a plasmid vector, such as a Bluescript plasmid (available from Stratagene, Inc., La Jolla, Calif.). The recombinant vector is then introduced into an *E. coli* strain (such as *E. coli* XL1-Blue, also available from Stratagene, Inc.) and the protein encoded by the cDNA is expressed in *E. coli* and then purified. For example, *E. coli* XL 1-Blue harboring a Bluescript vector including a cDNA molecule of interest can be grown overnight at 37° C. in LB medium containing 100 µg ampicillin/ml. A 50 µl aliquot of the overnight culture can be used to inoculate 5 mg of fresh LB medium containing ampicillin, and the culture grown at 37° C. with vigorous agitation to $A_{600}$=0.5 before induction with 1 mM IPTG.

After an additional two hours of growth, the suspension is centrifuged (1000×g, 15 min, 4° C.), the media removed, and the pelleted cells resuspended in 1 ml of cold buffer that preferably contains 1 mM EDTA and one or more proteinase inhibitors. The cells can be disrupted by sonication with a microprobe. The chilled sonicate is cleared by centrifugation and the expressed, recombinant protein purified from the supernatant by art-recognized protein purification techniques, such as those disclosed in Methods in Enzymology, Vol. 182, Guide to Protein Purification, Murray P. Deutscher, ed (1990), which publication is incorporated herein by reference.

Methods for preparing monoclonal and polyclonal antibodies are well known to those of ordinary skill in the art and are set forth, for example, in chapters five and six of *Antibodies A Laboratory Manual*, E. Harlow and D. Lane, Cold Spring Harbor Laboratory (1988), the cited chapters of which are incorporated herein by reference. In one representative example, polyclonal antibodies specific for a purified protein can be raised in a New Zealand rabbit implanted with a whiffle ball. One µg of protein is injected at intervals directly into the whiffle ball granuloma. A representative injection regime is injections (each of 1 µg protein) at day 1, day 14 and day 35. Granuloma fluid is withdrawn one week prior to the first injection (preimmune serum), and forty days after the final injection (postimmune serum).

Sequence variants, produced by deletions, substitutions, mutations and/or insertions, of the transcription factors useful in the practice of the present invention can also be used in the methods of the present invention. The amino acid sequence variants of the transcription factors useful in the practice of the present invention may be constructed by mutating the DNA sequences that encode the wild-type transcription factor proteins, such as by using techniques commonly referred to as site-directed mutagenesis. Nucleic acid molecules encoding the transcription factors useful in the practice of the present invention can be mutated by a variety of PCR techniques well known to one of ordinary skill in the art. (See, for example, the following publications, the cited portions of which are incorporated by reference herein: "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, N.Y. (1990)).

By way of non-limiting example, the two primer system utilized in the Transformer Site-Directed Mutagenesis kit from Clontech, may be employed for introducing site-directed mutants into nucleic acid molecules encoding transcription factors useful in the practice of the present invention. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be fully sequenced or restricted and analyzed by electrophoresis on Mutation Detection Enhancement gel (J. T. Baker) to confirm that no other alterations in the sequence have occurred (by band shift comparison to the unmutagenized control).

Again, by way of non-limiting example, the two primer system utilized in the QuikChange™ Site-Directed Mutagenesis kit from Stratagene (La Jolla, Calif.), may be employed for introducing site-directed mutants into nucleic acid molecules encoding transcription factors useful in the practice of the present invention. Double-stranded plasmid DNA, containing the insert bearing the target mutation site, is denatured and mixed with two oligonucleotides complementary to each of the strands of the plasmid DNA at the target mutation site. The annealed oligonucleotide primers are extended using Pfu DNA polymerase, thereby generating a mutated plasmid containing staggered nicks. After temperature cycling, the unmutated, parental DNA template is digested with restriction enzyme DpnI which cleaves methylated or hemimethylated DNA, but which does not cleave unmethylated DNA. The parental, template DNA is almost always methylated or hemimethylated since most strains of E. coli, from which the template DNA is obtained, contain the required methylase activity. The remaining, annealed vector DNA incorporating the desired mutation(s) is transformed into E. coli.

In the design of a particular site directed mutagenesis experiment, it is generally desirable to first make a non-conservative substitution (e.g., Ala for Cys, His or Glu) and determine if activity is greatly impaired as a consequence. If the residue is by this means demonstrated to be important by activity impairment, or knockout, then conservative substitutions can be made, such as Asp for Glu to alter side chain length, Ser for Cys, or Arg for His. For hydrophobic segments, it is largely size that is usefully altered, although aromatics can also be substituted for alkyl side chains.

Other site directed mutagenesis techniques may also be employed with nucleic acid molecules encoding transcription factors useful in the practice of the present invention. For example, restriction endonuclease digestion of DNA followed by ligation may be used to generate deletion variants of transcription factors useful in the practice of the present invention, as described in Section 15.3 of Sambrook et al. *Molecular Cloning: A Laboratory Manual*, 2nd Ed., Cold Spring Harbor Laboratory Press, New York, N.Y. (1989), incorporated herein by reference. A similar strategy may be used to construct insertion variants, as described in section 15.3 of Sambrook et al., supra.

Oligonucleotide-directed mutagenesis may also be employed for preparing substitution variants of transcription factors useful in the practice of the present invention. It may also be used to conveniently prepare the deletion and insertion variants of transcription factors useful in the practice of the present invention. This technique is well known in the art as described by Adelman et al. (*DNA* 2:183 [1983]); Sambrook et al., supra; "Current Protocols in Molecular Biology", 1991, Wiley (NY), F. T. Ausubel, R. Brent, R. E. Kingston, D. D. Moore, J. D. Seidman, J. A. Smith and K. Struhl, eds., incorporated herein by reference.

Generally, oligonucleotides of at least 25 nucleotides in length are used to insert, delete or substitute two or more nucleotides in the nucleic acid molecules encoding transcription factors useful in the practice of the present invention. An optimal oligonucleotide will have 12 to 15 perfectly matched nucleotides on either side of the nucleotides coding for the mutation. To mutagenize wild-type transcription factor proteins useful in the practice of the present invention, the oligonucleotide is annealed to the single-stranded DNA template molecule under suitable hybridization conditions. A DNA polymerizing enzyme, usually the Klenow fragment of E. coli. DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type protein inserted in the vector, and the second strand of DNA encodes the mutated form of the protein inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type protein DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Prokaryotes may be used as host cells for the initial cloning steps of transcription factors useful in the practice of the present invention. They are particularly useful for rapid production of large amounts of DNA, for production of single-stranded DNA templates used for site-directed mutagenesis, for screening many mutants and/or putative inner ear cell transcription factors simultaneously, and for DNA sequencing of the mutants generated. Suitable prokaryotic host cells include E. coli K12 strain 94 (ATCC No. 31,446), E. coli strain W3110 (ATCC No. 27,325) E. coli X1776 (ATCC No. 31,537), and E. coli B; however many other strains of E. coli, such as HB101, JM101, NM522, NM538, NM539, and many other species and genera of prokaryotes including bacilli such as Bacillus subtilis, other enterobacteriaceae such as Salmonella typhimurium or Serratia marcesans, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in *Genetic Engineering, Principles and Methods*, 12:275–296, Plenum Publishing Corp., 1990; Hanahan et al., *Meth. EnzyMol.* 204:63 (1991).

As will be apparent to those skilled in the art, any plasmid vectors containing replicon and control sequences that are derived from species compatible with the host cell may also be used to clone, express and/or manipulate nucleic acid molecules encoding transcription factors useful in the practice of the present invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI118, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl. Acids Res.* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

The construction of suitable vectors containing DNA encoding replication sequences, regulatory sequences, phenotypic selection genes and the DNA encoding a transcription factor useful in the practice of the present invention are prepared using standard recombinant DNA procedures. Isolated plasmids and DNA fragments are cleaved, tailored, and ligated together in a specific order to generate the desired vectors, as is well known in the art (see, for example, Sambrook et al., supra).

In another embodiment of the methods of the present invention, the formation of inner ear sensory hair cells from inner ear support cells is stimulated by damaging inner ear sensory hair cells and inhibiting the expression (before, during and/or after damaging the inner ear sensory hair cells) of one or more cell cycle inhibitors active in inner ear support cells. In this way, inner ear support cells that are in contact with damaged sensory hair cells can be stimulated to divide and at least some of the resulting progeny form inner ear sensory hair cells. By way of representative example, cell cycle inhibitors active in inner ear support cells include cyclin-dependent kinase inhibitors, such as cyclin-dependent kinase inhibitors of the so-called CIP/KIP family including $p21^{Cip1}$, $p27^{Kip1}$ and $p57^{Kip2}$.

Specific examples of cell cycle inhibitors active within inner ear support cells include: $p57^{Kip2}$ (Lee et al., *Genes Dev.* 9(6):639–649 (1995)(SEQ ID NO:6)); $p27^{Kip1}$ (*Cell* 78(1):59–66 (1994)(SEQ ID NOS:8 and 9)); $p21^{Cip1}$ (El-Diery et al., *Cell* 75(4):817–825 (1993)(SEQ ID NOS:10 and 11)); p19 Ink 4d (Chan et al., *Mol. Cell. Biol.* 15(5): 2682–2688 (1995)(SEQ ID NOS:12 and 13)); p18 Ink 4c (Guan et al., *Genes Dev.* 8(24):2939–2952 (1994)(SEQ ID NOS:14 and 15)); p15 Ink 4b (Hannon and Beach, 371 (6494):257–261 (1994)(SEQ ID NOS:16 and 17)); and p16 Ink 4a (Serrano, M. et al., *Nature* 366(6456):704–707 (1993)(SEQ ID NOS:18 and 19)). Nucleic acid molecules that encode cell cycle inhibitors useful in the practice of the present invention hybridize to the antisense strands of any one of the nucleic acid molecules set forth in SEQ ID NOS: 6, 8, 10, 12, 14, 16 and 18 under at least one hybridization stringency greater than 2×SSC at 55° C., such as 1×SSC at 60° C., or 0.2×SSC at 60° C.

Inhibitors of cell cycle inhibitors can be substances, such as proteins, that act on the cell cycle inhibitor in an intracellular, direct or indirect manner. Additionally, inhibitors of cell cycle inhibitors can be antisense nucleic acid molecules that are complementary to all or a portion of a nucleic acid molecule (such as an mRNA molecule) that encodes a cell cycle inhibitor protein, and that hybridize to the nucleic acid molecule encoding a cell cycle inhibitor protein under stringent conditions (such as a stringency greater than 2×SSC at 55° C., e.g., 1×SSC at 60° C. or 0.2×SSC at 60° C.).

Any art-recognized method can be used to inhibit cell cycle inhibitor gene expression in inner ear support cells. For example, the expression of a cell cycle inhibitor active in inner ear support cells can be inhibited by introducing into inner ear support cells a vector that includes a portion (or all) of a nucleic acid molecule, in antisense orientation relative to a promoter sequence, that encodes a cell cycle inhibitor active in inner ear support cells.

In general, antisense technology utilizes a DNA sequence that is inverted relative to its normal orientation for transcription and so expresses an RNA transcript that is complementary to a target mRNA molecule expressed within the host cell (i.e., the RNA transcript of the anti-sense gene can hybridize to the target mRNA molecule through Watson-Crick base pairing). An anti-sense gene may be constructed in a number of different ways provided that it is capable of interfering with the expression of a target gene, such as a gene encoding a cell cycle inhibitor. The anti-sense gene can be constructed by inverting the coding region (or a portion thereof) of the target gene relative to its normal orientation for transcription to allow the transcription of its complement, hence the RNAs encoded by the anti-sense and sense gene are complementary.

The anti-sense gene generally will be substantially identical to at least a portion of the target gene or genes. The sequence, however, need not be perfectly identical to inhibit expression. Generally, higher homology can be used to compensate for the use of a shorter anti-sense gene. The minimal identity will typically be greater than about 65%, but a higher identity might exert a more effective repression of expression of the endogenous sequences. Substantially greater identity of more than about 80% is preferred, though about 95% to absolute identity would be most preferred.

Furthermore, the anti-sense gene need not have the same intron or exon pattern as the target gene, and non-coding segments of the target gene may be equally effective in achieving anti-sense suppression of target gene expression as coding segments. Normally, a DNA sequence of at least about 30 or 40 nucleotides should be used as the anti-sense gene, although a longer sequence is preferable. The construct is then introduced into one or more inner ear support cells and the antisense strand of RNA is produced.

Catalytic RNA molecules or ribozymes can also be used to inhibit expression of target genes. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs. Tabler et al. (1991, *Gene* 108: 175) have greatly simplified the construction of catalytic RNAs by combining the advantages of the anti-sense RNA and the ribozyme technologies in a single construct. Smaller regions of homology are required for ribozyme catalysis, therefore this can promote the repression of different members of a large gene family if the cleavage sites are conserved.

An additional strategy suitable for suppression of target gene activity entails the sense expression of a mutated or partially deleted form of the protein encoded by the target gene according to general criteria for the production of dominant negative mutations (Herskowitz I, *Nature* 329: 219–222 (1987)).

Any art-recognized gene delivery method can be used to introduce a nucleic acid molecule encoding a transcription factor (or a vector including an antisense DNA molecule) into inner ear cells for expression therein, including: direct injection, electroporation, virus-mediated gene delivery, amino acid-mediated gene delivery, biolistic gene delivery, lipofection and heat shock. Non-viral methods of gene delivery into inner ear cells are disclosed in Huang, L., Hung, M-C, and Wagner, E., Non-Viral Vectors for Gene Therapy, Academic Press, San Diego, Calif. (1999), which is incorporated herein by reference.

For example, genes can be introduced into cells in situ, or after removal of the cells from the body, by means of viral vectors. For example, retroviruses are RNA viruses that have the ability to insert their genes into host cell chromosomes after infection. Retroviral vectors have been developed that lack the genes encoding viral proteins, but retain the ability to infect cells and insert their genes into the chromosomes of the target cell (A. D. Miller, *Hum. Gen. Ther.* 1:5–14 (1990)).

Adenoviral vectors are designed to be administered directly to patients. Unlike retroviral vectors, adenoviral vectors do not integrate into the chromosome of the host cell. Instead, genes introduced into cells using adenoviral vectors are maintained in the nucleus as an extrachromosomal element (episome) that persists for a limited time period. Adenoviral vectors will infect dividing and non-dividing cells in many different tissues in vivo including airway epithelial cells, endothelial cells, hepatocytes and various tumors (B. C. Trapnell, *Adv Drug Del Rev.* 12:185–199 (1993)).

Another viral vector is the herpes simplex virus, a large, double-stranded DNA virus that has been used in some initial applications to deliver therapeutic genes to neurons and could potentially be used to deliver therapeutic genes to some forms of brain cancer (D. S. Latchman, *Mol. Biotechnol.* 2:179–95 (1994)). Recombinant forms of the vaccinia virus can accommodate large inserts and are generated by homologous recombination. To date, this vector has been used to deliver interleukins (ILs), such as human IL-1β and the costimulatory molecules B7-1 and B7-2 (G. R. Peplinski et al., *Ann. Surg. Oncol.* 2:151–9 (1995); J. W. Hodge et al., *Cancer Res.* 54:5552–55 (1994)).

Another approach to gene therapy involves the direct introduction of DNA plasmids into patients. (F. D. Ledley, *Hum. Gene Ther.* 6:1129–1144 (1995)). The plasmid DNA is taken up by cells within the body and can direct expression of recombinant proteins. Typically plasmid DNA is delivered to cells in the form of liposomes in which the DNA is associated with one or more lipids, such as DOTMA (1,2,-diolcyloxypropyl-3-trimethyl ammonium bromide) and DOPE (dioleoylphosphatidylethanolamine). Formulations with DOTMA have been shown to provide expression in pulmonary epithelial cells in animal models (K. L. Brigham et al., *Am. J. Med. Sci.* 298:278–281 (1989); A. B. Canonico et al., *Am. J. Respir. Cell. Mol. Biol.* 10:24–29 (1994)). Additionally, studies have demonstrated that intramuscular injection of plasmid DNA formulated with 5% PVP (50,000 kDa) increases the level of reporter gene expression in muscle as much as 200-fold over the levels found with injection of DNA in saline alone (R. J. Mumper et al., *Pharm. Res.* 13:701–709 (1996); R. J. Mumper et al., *Proc. Intern. Symp. Cont. Rol. Bioac. Mater.* 22:325–326 (1995)). Intramuscular administration of plasmid DNA results in gene expression that lasts for many months (J. A. Wolff et al., *Hum. Mol. Genet.* 1:363–369 (1992); M. Manthorpe et al., *Hum. Gene Ther.* 4:419–431 (1993); G. Ascadi et al., *New Biol.* 3:71–81 (1991), D. Gal et al., *Lab. Invest.* 68:18–25 (1993)).

Additionally, uptake and expression of DNA has also been observed after direct injection of plasmid into the thyroid (M. Sikes et al., *Hum. Gene Ther.* 5:837–844 (1994)) and synovium (J. Yovandich et al., *Hum. Gene Ther.* 6:603–610 (1995)). Lower levels of gene expression have been observed after interstitial injection into liver (M. A. Hickman et al., *Hum. Gene Ther.* 5:1477–1483 (1994)), skin (E. Raz et al., *Proc. Natl. Acad. Sci.* 91:9519–9523 (1994)), instillation into the airways (K. B. Meyer et al., *Gene Therapy* 2:450–460 (1995)), application to the endothelium (G. D. Chapman et al., *Circulation Res.* 71:27–33 (1992); R. Riessen et al., *Human Gene Therapy* 4:749–758 (1993)), and after intravenous administration (R. M. Conry et al., *Cancer Res.* 54:1164–1168 (1994)).

Various devices have been developed for enhancing the availability of DNA to the target cell. A simple approach is to contact the target cell physically with catheters or implantable materials containing DNA (G. D. Chapman et al., *Circulation Res.* 71:27–33 (1992)). Another approach is to utilize needle-free, jet injection devices which project a column of liquid directly into the target tissue under high pressure. (P. A. Furth et al., *Anal Biochem.* 20:365–368 (1992); (H. L. Vahlsing et al., *J. Immunol. Meth.* 175:11–22 (1994); (F. D. Ledley et al., *Cell Biochem.* 18A:226 (1994)).

Another device for gene delivery is the "gene gun" or Biolistic™, a ballistic device that projects DNA-coated micro-particles directly into the nucleus of cells in vivo. Once within the nucleus, the DNA dissolves from the gold or tungsten microparticle and can be expressed by the target cell. This method has been used effectively to transfer genes directly into the skin, liver and muscle (N. S. Yang et al., *Proc. Natl. Acad. Sci.* 87:9568–9572 (1990); L. Cheng et al., *Proc. Natl. Acad. Sci. USA.* 90:4455–4459 (1993); R. S. Williams et al., *Proc. Natl. Acad. Sci.* 88:2726–2730 (1991)).

Cochleostomy involves puncturing the cochlea and inserting a catheter through which a chemical agent, such as a nucleic acid molecule, can be introduced into the cochlea. A cochleostomy method is disclosed, for example, in Lalwani, A. K. et al., Hearing Research 114:139–147 (1997), which publication is incorporated herein by reference.

Another approach to targeted gene delivery is the use of molecular conjugates, which consist of protein or synthetic ligands to which a nucleic acid- or DNA-binding agent has been attached for the specific targeting of nucleic acids to cells (R. J. Cristiano et al., *Proc. Natl. Acad. Sci. USA* 90:11548–52 (1993); B. A. Bunnell et al., *Somat. Call Mol. Genet.* 18:559–69 (1992); M. Cotten et al., *Proc. Natl. Acad. Sci. USA* 89:6094–98 (1992)). Once the DNA is coupled to the molecular conjugate, a protein-DNA complex results. This gene delivery system has been shown to be capable of targeted delivery to many cell types through the use of different ligands (R. J. Cristiano et al., *Proc. Natl. Acad. Sci. USA* 90:11548–52 (1993)). For example, the vitamin folate has been used as a ligand to promote delivery of plasmid DNA into cells that overexpress the folate receptor (e.g., ovarian carcinoma cells) (S. Gottschalk et al., *Gene Ther.* 1:185–91 (1994)). The malaria circumsporozoite protein has been used for the liver-specific delivery of genes under conditions in which ASOR receptor expression on hepatocytes is low, such as in cirrhosis, diabetes, and hepatocellular carcinoma (Z. Ding et al., *J. Biol. Chem.* 270:3667–76 (1995)). The overexpression of receptors for epidermal growth factor (EGF) on cancer cells has allowed for specific uptake of EGF/DNA complexes by lung cancer cells (R. Cristiano et al., *Cancer Gene Ther.* 3:4–10 (1996)). The presently preferred gene delivery method is lipofection.

When the methods of the present invention are utilized in vitro, the whole inner ear, including the Organ of Corti, is preferably excised and cultured and manipulated in a culture vessel. Presently preferred embodiments of an apparatus that is useful for culturing inner ears in vitro are disclosed in U.S. patent No. 5,437,998; U.S. Pat. No. 5,702,941 and U.S. Pat. Ser. No. 5,763,279, each of which is incorporated herein by reference.

In general, presently preferred embodiments of an apparatus for culturing inner ears include a gas permeable bioreactor comprising a tubular vessel with walls that may be constructed at least partially of a gas permeable material, such as silicone rubber. The vessel in one preferred embodiment is constructed such that half of it is comprised of gas permeable material and the remaining portion is made of nonpermeable material. The gas permeable materials commonly available are opaque. Thus, using nonpermeable material for at least part of the bioreactor may provide an advantage in allowing visual inspection of the tubular vessel chamber.

The tubular vessel has closed ends, a substantially horizontal longitudinal central axis, and one or more vessel access ports. The vessel access ports provide access to the bioreactor for input of medium and cells, and for removal of old medium from the tubular vessel. This is easily done through the vessel access ports which are also referred to as valves or syringe ports. In the preferred embodiment, the vessel access ports are constructed of valves with syringe ports.

Preferably the vessel is rotatable about its horizontal longitudinal central axis. A preferred means for rotation is a motor assembly which sits on a mounting base and has means for attachment to the tubular vessel. The speed of rotation can be adjusted so that the inner ear within the tubular vessel is constantly in motion, but rotation of the tubular vessel should not be fast enough to cause significant turbulence in the aqueous medium within the tubular vessel.

If so desired, the use of gas permeable material in the construction of at least part of the tubular vessel wall permits $O_2$ to diffuse through the vessel walls and into the cell culture media in the vessel chamber. Correspondingly, $CO_2$ diffuses through the walls and out of the vessel. Thus, the use of gas permeable material in the construction of at least part of the tubular vessel wall typically overcomes the need for air injection into the bioreactor vessel. Air injection into the aqueous medium within the bioreactor vessel may be utilized, however, if additional oxygen is required to culture an inner ear. When an air pump is utilized to inject air into the aqueous medium, an air filter is also employed to protect the air pump valves from dirt.

An alternative embodiment of the bioreactor useful in the practice of the present invention is an annular vessel with walls that may be constructed at least partially of a gas permeable material. Annular is defined herein to include annular, toroidal and other substantially symmetrical ring-like shaped tubular vessels. The annular vessel has closed ends and a substantially horizontal longitudinal central axis.

In another embodiment, the bioreactor useful in the practice of the present invention comprises a tubular vessel constructed at least partially of a gas permeable material. The vessel has closed ends and a substantially horizontal longitudinal central axis around which it rotates. The vessel furthermore has two slidably interconnected members wherein a first member fits slidably into a second member, forming a liquid tight seal therebetween and providing a variable volume tubular vessel. The bioreactor has means for rotating the tubular vessel about its substantially horizontal longitudinal central axis. One or more vessel access ports are provided for transferring materials into and out of the vessel.

In situations where minimization of contamination is necessary (e.g., AIDS or human tissue research), disposability of the bioreactor useful in the practice of the present invention is a particular advantage. Moreover, the embodiment of the bioreactor with slidably interconnected members may be adjusted to provide the exact size bioreactor needed.

Presently preferred, commercially available bioreactors useful in the practice of the present invention for culturing fluid-filled sensory organs are known as the High Aspect Ratio Vessel (HARV™) and the Cylindrical Cell Culture Vessel (CCCV™) and are manufactured by Synthecon, Inc. (8054 El Rio, Houston, Tex.).

Neuralbasal™ media from Gibco BRL (Gibco BRL media are produced by Life Technologies, Corporate Headquarters, Gaithersburg, Md.), which requires the addition of B27 or N2 media supplement, is the presently preferred culture medium for culturing inner ears in vitro. Other culture media can be successfully used, however, to culture fluid-filled sensory organs in the practice of the present invention. Other suitable media include DME, BME and M-199 with fetal calf serum or horse serum. All of the foregoing media are sold by Gibco -BRL. When using Neuralbasal™ medium, N2 or B27 supplements play a more significant role when extended periods of culture (>96 hr) are attempted.

In another aspect, the present invention provides methods for stimulating the formation of inner ear support cells. The methods of this aspect of the invention include the steps of damaging inner ear support cells under conditions that promote the formation of new inner ear support cells (for example by cell division of inner ear support cells that are in contact with damaged inner ear support cells). In this aspect of the invention, the inner ear support cell is damaged, and the formation of new inner ear support cells is stimulated, using the same techniques described herein for the methods of the present invention that stimulate the formation of inner ear sensory hair cells from inner ear support cells. Thus, for example, inner ear support cells can be damaged by contact with an amount of an ototoxic agent, such as an aminoglycoside antibiotic, that is effective to damage inner ear support cells. Again by way of example, new inner ear support cell formation can be further stimulated by damaging inner ear support cells and expressing (before, during and/or after damaging inner ear support cells) within inner ear support cells a transcription factor (such as POU4F1, POU4F2, POU4F3, Brn3a, Brn3b and Brn3c) capable of stimulating inner ear support cells to divide and form new inner ear support cells. In preferred embodiments of this aspect of the invention, the proliferation of inner ear support cells results in improvement in the auditory function of the treated inner ear.

The following examples merely illustrate the best mode now contemplated for practicing the invention, but should not be construed to limit the invention.

EXAMPLE 1

Overexpressing POU4F3 in Immortalized Supporting-Cell Lines In Vitro.

POU4F3 is a DNA binding transcription factor exhibiting remarkable specificity to the hair-cells in the inner ear. Mutations in POU4F3 are known to cause developmental failures in mice, and hearing loss in both mice and humans. The role of POU4F3 in directing the development of hair-cell precursors is investigated by transfecting inner ear supporting-cell lines with POU4F3.

To detect the expression of POU4F3 in live cultures, the expression of Enhanced Green Fluorescent Protein (EGFP), translated from a bicistronic mRNA which includes both POU4F3 and GFP coding regions, is monitored. Specifically, a 1250 bp cDNA encoding POU4F3 including 70 bp of 5'UTR and 73 bp of 3'UTR is directionally cloned into the unique EcoRV restriction site of the pIRES2-EGFP vector (Clonetech) directly down stream from the human CMV major immediate early promoter/enhancer. An intervening synthetic intron is cloned downstream from the POU4F3 gene to enhance the stability of the mRNA. The internal ribosomal entry site (IRES) from encephelomyocarditis virus is cloned between the POU4F3 gene and the GFP gene to allow for the translation of GFP and POU4F3 protein from the same mRNA. Immediately following the GFP coding region is a poly-adenylation signal from the bovine growth hormone gene. This expression cassette is designed to take advantage of the bicistronic promoter to allow tracking of transfection and expression of POU4F3 and GFP by visualization of expressed GFP under fluorescence microscopy. This second generation GFP vector has a red shifted variant of wild-type GFP (Excitation maximum=488 nm; emission maximum=507 nm) which has been optimized for brighter fluorescence. To optimize the identification of cells expressing high levels of the POU4F3 protein, the pIRES2 vector utilizes a partially disabled IRES sequence (Rees, S. et al., BioTechniques 20:102110 (1996)). This attenuated IRES leads to a reduced rate of translation initiation at the GFP start codon relative to that of the POU4F3 gene.

The supporting-cell line (UCL) was established from the inner ear vestibular sensory epithelia of the 112k$^b$-tsA 58 transgenic mouse (Immortamouse). Utricles from postnatal day one mice were dissected and the sensory epithelia (hair-cells and supporting-cells) isolated after brief thermolysin treatment at 37° C. The resultant supporting-cell line was derived after several passages at permissive conditions (33° C. and γINF) which stimulates rapid cell proliferation. Confluence was achieved in 3–4 days. This process resulted in the death of all hair-cells as determined by ICC and electron microscopy (EM). The UCLs were further characterized by an antibody called ZO-1 (which labels tight junctions that are present in supporting-cells) and EM (which showed tight junction complexes, secretory vesicles and luminal surface microvilli, all characteristic of supporting-cells).

Culture medium for the UCL cell line consisted of DMEM/F12 (Gibco), fetal bovine serum (10%) and γINF (20 u/ml). Media changes were done 2 to 3 times a week depending on the growth rate of the cells. Single-cell clones were developed using a special seeding method that enabled single cells to become confluent and passageable in 3–4 weeks. At non-permissive conditions (37° C. or 39° C., no γINF and low or no FBS) cell growth arrests.

Given the high transfection efficiencies already observed in the UCLs, these cells are grown and passaged in defined media that is serum free. Once this is established, these cells are lipofected with the IRES-GFP-POU4F3 encoding plasmid. Cultures are monitored for GFP expression over 1–6 DIV. When periods of high GFP fluorescence are observed in live cultures, the culture are fixed and prepared for POU4F3 and calbindin ICC.

EXAMPLE 2

Overexpression of POU4F3 in Lesioned Organ of Corti Cultures.

Cultures from P7-P14 mice are established and lesioned with 1 mM neomycin for 2 DIV. The media are removed and the cultures lipofected with pIRES2-GFP-POU4F3 for 6 hr and recovered in fresh media for 1–6 DIV. Cultures are aldehyde-fixed and processed for POU4F3 and calbindin immunocytochemistry. pIRES2-GFP only lipofected cultures serve as controls. The presence of a triple labeled cell (positive for GFP, POU4F3, and calbindin immunoreactivity) indicates that POU4F3 is capable of promoting the adoption of a hair-cell phenotype in the lesioned organ of Corti. Further determination of this phenotype is corroborated with antibodies against other hair-cell selective markers such as myosin 6 and myosin 7a using polyclonal antibodies derived against these proteins.

Expression of hair-cell specific markers such as myosin 6 and 7a are observed in the embryonic mouse organ of Corti at E16, 2–3 days after the expression of the Brn 3.1 transcription factor begins at E13.5.

EXAMPLE 3

Regeneration of Inner Ear Hair Cells in p27$^{Kip1}$ −/− Mice

Previous reports in p27$^{Kip1}$ −/− and +/− mice showed qualitative evidence of supernumerary hair cells (HCs) in both inner hair cell (IHC) and outer hair cell (OHC) regions (Chen, P., & Segil, N. Development 126:1581–1590 (1999); Lowenheim, H., et al., Proc. Natl. Acad. Sci. USA. 96:4084–4088 (1999)). Unfortunately, the significant dysplasia of the surrounding supporting cells could very well account for some if not all of these observations. Therefore, the number of IHCs and OHCs in the cochlea of p27$^{Kip1}$ −/−, +/− and +/+ mice was measured. To more accurately assess whether there was a true increase in HC number, several regions from the same cochlea were analyzed. Using a HC specific marker, a myosin-VIIa antibody, a 20% increase in the number of IHCs in p27$^{Kip1}$ −/− cochlea was observed when compared with that in p27$^{Kip1}$ +/− and +/+ cochlea. However, there was no statistically significant difference in the overall number of OHCs between p27$^{Kip1}$ −/−, +/− and +/+ cochlea, except for a 10% increase in the number of OHCs in one analyzed region (Table 1). Table 1 shows the number of hair cells (n) in four-week old p27$^{Kip1}$ +/+, +/−, −/− mice. Counts were made from a 100 μm length of sensory epithelium from three different locations along the longitudinal axis of the organ of Corti. Distance corresponds to degrees from the apical tip of the cochlea (±s.d.). Comparisons were made with the same hair cell region across +/+, +/− and −/−. Statistical significance was determined using ANOVA.

TABLE 1

| Genotype | Distance | n | IHC | OHC |
| --- | --- | --- | --- | --- |
| +/+ | 90 | 6 | 13.0 ± 0.0 | 42.8 ± 2.5 |
| +/− | 90 | 16 | 13.1 ± 0.7 | 44.1 ± 2.9 |
| −/− | 90 | 11 | 16.0 ± 1.9* | 43.5 ± 2.3 |
| +/+ | 180 | 6 | 13.3 ± 0.8 | 40.5 ± 5.2 |
| +/− | 180 | 16 | 13.2 ± 0.8 | 43.1 ± 2.2 |
| −/− | 180 | 11 | 17.0 ± 1.3* | 45.9 ± 3.3* |
| +/+ | 360 | 6 | 13.7 ± 0.8 | 41.7 ± 5.1 |
| +/− | 360 | 16 | 13.4 ± 0.5 | 43.1 ± 2.8 |
| −/− | 360 | 11 | 16.2 ± 1.8* | 41.0 ± 4.6 |

*p-value < .001

To determine whether auditory hair cells were being produced after the onset of hearing at postnatal day 10, two-week old p27$^{Kip1}$ −/−, +/−, +/+ mice (P10–12) received three daily systemic injections of bromodeoxyuridine (BrdU; 30mg/kg/s.c), a nucleotide analog which is incorporated into proliferating cells during S phase. Mice were then permitted to recover for two-days or two-weeks without further injections. BrdU positive HCs were identified with immunocytochemistry using light and fluorescence microscopy. Cochlea were also labeled with antibodies against myosin-VI and myosin-VIIa. In two-week old p27$^{Kip1}$ −/− cochlea that were recovered for 2d after the last injection, no BrdU/myosin-VIIa positive cells were observed among the BrdU positive cells. However, in four-week old p27$^{Kip1}$ −/− cochlea that were recovered for 14 days after the last injection, BrdU/myosin-VIIa positive HCs were observed. Most of those double labeled were IHCs. This qualitative finding is similar to our quantitative assessments of IHCs and OHCs numbers. p27$^{Kip1}$ +/−, +/+ mice were completely devoid of BrdU positive cells at 2d and 14d of recovery. These data are summarized in Table 2. Table 2 shows the number (n) of BrdU labeled cells in the organ of Corti of two- and four-week old p27$^{Kip1}$ +/+, +/−, −/− mice injected with BrdU or BrdU/Amikacin with 2d or 14d of recovery. Counts were performed on a 1000 μm length of sensory epithelium taken in the apical half of the cochlea (±s.d.). Proliferation in the BrdU groups were compared across +/+, +/− and −/−. Proliferation in the BrdU/Amikacin group was compared with that in the BrdU only group of the same genotype. Statistical significance was determined using ANOVA.

TABLE 2

| Genotype | n | BrdU + 2d | n | BrdU/Amikacin + 2d |
| --- | --- | --- | --- | --- |
| +/+ | 10 | 0.0 ± 0.0 | | 0.0 ± 0.0 |
| +/− | 12 | 0.0 ± 0.0 | | 4.7 ± 7.6 |
| −/− | 4 | 82.3 ± 11.0* | | 96.3 ± 9.5 |

TABLE 2-continued

| Genotype | n | BrdU + 14d | n | BrdU/Amikacin + 14d |
| --- | --- | --- | --- | --- |
| +/+ | 10 | 0.0 ± 0.0 | 10 | 0.0 ± 0.0 |
| +/− | 18 | 0.0 ± 0.0 | 10 | 10.5 ± 12.0* |
| −/− | 6 | 82.2 ± 22.5* | 12 | 137.4 ± 17.0* |

*p-value < .001

To ascertain whether auditory HCs could be regenerated, HCs were lesioned using systemic injections of amikacin sulfate (P7-P2) and then injected with BrdU (P10–12). Mice were sacrificed either 2 d or 14 d after the last injection. The effects of an amikacin lesioning were at least two-fold. First, in both p27$^{Kip1}$ −/− and +/− mice, the number of BrdU positive cells increased following amikacin/BrdU vs BrdU alone treatment. In p27$^{Kip1}$ +/− cochlea, the numbers of BrdU labeled cells increased in the majority of specimens examined, however, not all p27$^{Kip1}$ +/− cochlea displayed BrdU positive cells. Evidence of HC regeneration was confirmed by sectioning the labeled cochlea. Second, a greater number of BrdU positive HCs were observed following amikacin lesioning in p27$^{Kip1}$ −/− cochlea. The majority of the BrdU positive HCs appeared in the regions of the cochlea where the amikacin sulfate had injured or killed HCs (in the basal half of the cochlea). No BrdU positive cells were observed in wt cochlea following amikacin/BrdU or BrdU alone treatment. These data are summarized in Table 2.

To measure specific protein levels, single cochlear lysates were serially diluted and run on polyacrylamide gels. Western blotting showed that myosin-VI and VIIa levels appeared roughly equal across p27$^{Kip1}$ −/−, +/− and +/+ cochlea, although a stronger myosin-VIIa band was observed from p27$^{Kip1}$ −/− cochlea. p27$^{Kip1}$ +/− cochlea contained approximately 50% of the p27$^{Kip1}$ protein levels found in wt cochlea, indicating that a reduction of p27$^{Kip1}$ to 50% of normal can stimulate supporting cell proliferation and allow some hair cell regeneration to occur following amikacin sulfate treatment.

The protocol used to measure protein levels in the cochlea is as follows. A cochlea is transferred to a tube with 10 μl of extraction buffer which contains:HEPES (25 mM), NP-40 (0.7%), Aprotintin (1 mM), Leupeptin (1 μg/ml), Pepstatin (10 μM), phenylmethylsulfonylfluoride (PMSF) (1 mM), dithiothreitol (DTT) (1 mM), and ethylenediaminetetraacetic acid (EDTA) (2 mM). The cochlea is homogenized immediately and the tube is placed on ice for about 30 min. Add 5 μl of 4× sample buffer and adjust the salt concentration up to 0.5 M. Heat up the sample to 90–100° C. for 5 min then spin at 13,000 rpm for 10 min and collect the supernatant. Aliquots of protein from the supernatant are run on a 15% SDS-PAGE gel for 50 min at 200 V and the proteins are transferred onto PVDF membrane for 1 hr at 100 V. The membrane is blocked with 10% Amersham blocking buffer for 1 hr or overnight. Primary antibody in blocking buffer is applied to the membrane for 1 hr and the membrane is then washed five times with PBS/Tween for 5 minutes per wash. The membrane is probed with goat anti-mouse or goat anti-rabbit-alkaline phosphatase plus anti-biotin-AP for 1 hr and washed five times with PBS/Tween for 5 minutes per wash.

To determine whether p27$^{Kip1}$ plays a similar role in the peripheral vestibular system, the proliferative capacity of the utricle, saccule and cristae of p27$^{Kip1}$ +/−, and +/+ mice was examined. Mice (P7-P12) received systemic injections of amikacin sulfate (500 mg/kg/d/s.c) for six consecutive days that were combined with injections of the replication marker, bromodeoxyuridine (BrdU; 30 mg/kg/d/s.c) between P10-P12. Mice were also injected with BrdU alone in a similar fashion. Mice were then sacrificed 14 d later and the vestibular sensory organs were fixed, dissected and processed for BrdU immunocytochemistry. BrdU positive nuclei were counted from whole mounts using light microscopy and Nomarski optics. Selected organs were further processed for cross section analysis.

In p27$^{Kip1}$ −/− mice that received BrdU only, very low levels of BrdU-labeled cells were observed in the saccule and utricle. However, after combined amikacin/BrdU treatment, a 40-fold increase in the number of BrdU positive cells was observed in both organs. Approximately one-half of the labeled cells appeared as doublets suggesting recent or ongoing cell divisions. Plastic cross sections showed that the majority of the BrdU labeled cells were in the basal layer of the sensory epithelium, along the basal membrane. BrdU positive HCs were also observed in both otolithic organs. Most of these regenerated HC appeared as type I HCs in that they were contacted by a calyx. In p27$^{Kip1}$ +/− mice that received BrdU only, no proliferation was observed in either the saccule or utricle. After combined amikacin/BrdU treatment, a very low level of proliferation was induced. In p27$^{Kip1}$ +/+ mice, no BrdU positive nuclei in either the saccule or utricle were observed after amikacin/BrdU or BrdU alone. Interestingly, no BrdU positive cells were observed in the cristae of any genotype following amikacin/BrdU or BrdU only. These data indicate significantly different effects in deleting p27$^{Kip1}$ among the various vestibular sensory organs and between the vestibular sensory organs and the organ of Corti. These data are summarized in Table 3. Table 3 shows the numbers of BrdU labeled cells in the vestibular organs of four-week old p27$^{Kip1}$ +/+, +/− and −/− mice injected with BrdU or BrdU/Amikacin and after a 14 d recovery. Counts were performed from whole utricular, saccular and cristae sensory epithelium (±s.d.). In the BrdU group, statistical significance was determined by comparing proliferation levels in the same sensory organ across +/+, +/− and −/−. In the BrdU/Amikacin group, statistical significance was determined by comparing proliferation levels in the same sensory organ of the same genotype. Statistical significance was determined using ANOVA.

TABLE 3

| | genotype | BrdU | BrdU/Amikacin |
|---|---|---|---|
| utricle (n) | | | |
| 8 | +/+ | 0.0 ± 0.0 | 0.0 ± 0.0 |
| 20 | +/− | 0.0 ± 0.0 | 0.4 ± 0.7 |
| 12 | −/− | 19.7 ± 13.4* | 45.5 ± 19.2* |
| saccule (n) | | | |
| 6 | +/+ | 0.0 ± 0.0 | 0.0 ± 0.0 |
| 16 | +/− | 0.0 ± 0.0 | 1.6 ± 1.9 |
| 9 | −/− | 32.7 ± 14.3* | 51.8 ± 15.3* |
| cristae (n) | | | |
| 12 | +/+ | 0.0 ± 0.0 | 0.0 ± 0.0 |
| 12 | +/− | 0.0 ± 0.0 | 0.0 ± 0.0 |
| 12 | −/− | 0.0 ± 0.0 | 0.0 ± 0.0 |

*p-value < .001

Selected semi-thin sections were re-embedded in plastic, thin sectioned and examined under electron microscopy. BrdU positive HCs displayed stereociliary bundles, cuticular plates, calyceal innervation with evidence of synapse formation.

EXAMPLE 4

Antisense Inhibition of p27$^{Kip1}$ Expression

To test whether inhibition of the p27$^{Kip1}$ gene product in p27$^{Kip1}$ +/+ cochlea would allow non-mitotic supporting cells to proliferate, wild type organ of Corti explants (P7-P10, at age of hearing onset) were treated with p27$^{Kip1}$ antisense oligonucleotides (ONs). Explant cultures were established by dissecting the organ of Corti from the cochlea, removing the tectorial membrane and adhering the organ of Corti to a glass slide coated with Cell-tak and maintained at 37° C. in a 5% $CO_2$ environment. The explant was then exposed to an ototoxic antibiotic (1 mM neomycin sulfate) for 48h which killed >95% of the HCs (Kil, J., et al., *ARO abs.* 21:672 (1998)). The neomycin containing media was then removed and p27$^{Kip1}$ antisense oligonucleotides (Ons) (40 nM) were administered using a cationic lipid (lipofection) for a period of 24–48 hr. Some of these living cultures were examined under fluorescence to detect the presence of FITC conjugated antisense ON.

FITC-positive supporting cells were detected in 18–24 h and increased in number and fluorescent intensity between 24–48 h. Cultures were aldehyde fixed and processed for BrdU immunocytochemistry. BrdU-positive supporting cells appeared in most cochlear cultures after 24 h of antisense oligonucleotide (ON) treatment. BrdU-positive doublets appeared in antisense ON treated cultures that were recovered for an additional 24 hr without antisense ONs. This indicated that successful completion of M phase and subsequent cell division could occur. Lipofection-only treated cultures contained very low levels of BrdU-labeled supporting cells.

We observed that administration of p27$^{Kip1}$ antisense oligonucleotides can induce supporting cells to proliferate in wild-type cochlea. This observation is unique and rather significant. Previous work demonstrating p27$^{Kip1}$ antisense ON induced proliferation were shown in actively dividing cells that had been transiently or reversibly growth arrested (Coats, S., et al, *Science*, 272:877–880 (1996); Dao, M. A., et al, *Proc. Natl. Acad. Sci. USA*, 95:13006–13011 (1998)). Our results are the first demonstration that terminally mitotic cells in a terminally differentiated organ can reenter the cell-cycle after inhibition of p27$^{Kip1}$ gene products.

Again, supporting cell proliferation normally ceases between E12–14 in the mouse organ of Corti. After this point, supporting cell differentiation continues through the second week of postnatal life. At the time of explant, cultures treated as described herein have already developed some adultlike morphologic characteristics. These data further support the role for p27$^{Kip1}$ antisense ON as a potential means for inducing hair cell regeneration. In p27$^{Kip1}$ +/− mice, a reduction to 50% of normal protein levels allows some terminally differentiated supporting cells to overcome the p27$^{Kip1}$ blockade and re-enter the cell cycle and proliferate.

The addition of growth factors that induce cell proliferation in other epithelial organs, does not promote cell proliferation or hair cell regeneration in the postnatal organ of Corti, either in vitro or in vivo. The experiments reported herein identify identified a rather ubiquitous and potent cell cycle inhibitor that, when deleted, allows the organ of Corti to regenerate some of its hair cells spontaneously. The organ of Corti of mice containing one copy of the gene and 50% of normal protein levels are capable of auditory hair cell regeneration.

In addition, organotypic cultures can be established on glass slides (Nunc) coated with CellTak (Collaborative Research) in 100 µls of NeuroBasal media (Gibco) containing 1 mM neomycin. This treatment kills 95% of the hair cells and also facilitates the level of transfection. Cultures are lipofected with antisense molecules using commercially available lipofection reagents (e.g, Perfect Lipofection Kit; InVitrogen, Inc.). The media also contains BrdU (10 µM) to identify proliferating cells. In addition, various recombinant growth factors such as TGF-alpha (1–100 nM), insulin (10–100 µM) and IGF-1 (1–100 µM) can be used to increase or drive this proliferative effect.

EXAMPLE 5

The Use of p27$^{Kip1}$ Antisense Oligonucleotides to Stimulate Cell Proliferation in a Guinea Pig Fibroblast Cell Line in Vitro Cultures of cell lines were established that are responsive to p27$^{Kip1}$ antisense oligonucleotides (ON) during the period of serum withdrawal and growth arrest. These cultures include a guinea pig fibroblast line (JH4). Lipofection of the 16 mer antisense ON (having the nucleic acid sequence set forth in SEQ ID NO:20) reversed growth arrest in the JH4 cell line to over 40% of normal.

EXAMPLE 6

Stimulation of Supporting Cell Proliferation in Guinea Pig Cochlea Using p27$^{Kip1}$ Antisense Molecules Two recent, independent studies indicate that antisense ONs can be successfully delivered through the perilymphatic space and elicit changes in the organ of Corti of mature guinea pigs (D'Aldin, C., et al., *Mol. Brain Res.*, 55:151–164 (1998); Leblanc, C. R., et al. *Hear. Res.*, 135: 105–112 (1999)). The presence of FITC-antisense ON against specific sequences to the mRNA of GluR2 was seen in the spiral ganglia, supporting cells, and inner and outer spiral sulcus cells within 24 h after the osmotic pump installation. A subsequent selective decrease in GluR2/3 protein was also observed in situ (D'Aldin et al., 1998, supra).

The expression pattern of p27$^{Kip1}$ in the mature guinea pig organ of Corti was found to be similar to that observed in developing and adult mice. Supporting cell proliferation in guinea pig cochlea is stimulated as follows:

General anesthesia is induced by inhalation of Isoflurane (5% for the induction and 2–3% for the maintenance) or by intramuscular injection of ketamine (50 mg/kg) and xylazine (9 mg/kg). 1% lidocaine is injected behind the pinna locally. The animal is placed on a warming pad to keep basal body temperature constant during the surgical operation. Respiration and circulation is monitored carefully. Drugs are delivered into the guinea pig's inner ear by surgically implanting an infusion unit which consists of a coiled catheter and an osmotic minipump (Alzet, cat no. 2002, 0.5 µl/h flow rate for up to 14 days). The coil is loaded with the drug and the osmotic minipump carries a dye. The total volume of drug pumped into the inner ear can be monitored by the amount of dye which is pumped into the coil. The drug is dissolved in a solution of artificial perilymph which consists of: 137 mM NaCl, 5 mM KCl, 2 mM CaCl$_2$, 1 mM MgCl$_2$, 10 mM Hepes, 11 mM Glucose, pH 7.4 and osmolarity 300 mOsm/L.

All surgical procedures are done under a dissection microscope and under sterile conditions. The mastoid bulla (middle ear space) is exposed via a post-auricular incision and opened using a 1 mm cutting burr to allow visualization of the basal turn of the cochlea. A cochleostomy about 1 mm inferior to the round window is fashioned using a 0.5 mm diamond paste burr. Observed inner ear perilymph fluid leaking from this site confirms correct positioning of the cochleostomy. The tip of the infusion unit is inserted into the cochleostomy and the tubing is secured on the wall of the middle ear by dental cement. The infusion unit is stored in a subcutaneous pocket created behind the neck. The skin incision is closed in layers with 2–0 silk. This procedure is performed on both ears to avoid any subsequent imbalance or rotational behavior and to reduce the number of animals needed to complete the experiment. The procedure takes approximately 30 minutes per side.

Repeat surgery for changing the infusion unit is done under general anesthesia one week after implantation. The procedure is done only through the initial post-auricular skin incision and does not involve re-entry into the middle ear space. This procedure takes 5–10 minutes per infusion unit. The post-surgical condition of the animal is monitored daily by checking activity, appetite, drinking, feces and body weight. The animal is sacrificed if it has lost more than 20% of its body weight post-surgery or exhibits severe rotational behavior or head tilt. No operative discomfort should occur and this procedure produces only slight postoperative discomfort.

As shown in Table 4 below, normal controls are given a solution of artificial perilymph for one or two weeks. The hair cell loss group receives gentamycin sulfate for one week to kill the hair cells with immediate sacrifice and two week recovery. Three concentrations are used that should provide a total loss of HCs as well as a graded loss of HCs. Cationic liposomes in 5% (w/v) dextrose solution are delivered for one to two weeks. The purpose of this group is to see if any damage is caused by lipofection. Lipofection after hair cell loss involves the substitution of a gentamycin containing pump to a lipid containing pump. Lipofection plus antisense after hair cell loss involves lipofecting FITC-antisense for another week. Lipofection plus antisense plus growth factors after damage are delivered for one week followed by the lipofection of antisense and growth factors for another week. Several groups involve combining antisense with growth factors, including TGF-alpha, insulin, and IGF-1. In all animals, a separate osmotic pump loaded with BrdU is implanted subcutaneously to allow identification of mitotically active cells

TABLE 4

| Animals (n) | Drugs (order) | Concentration (range) | Delivery time of drugs (d) Recovery time after (d) |
|---|---|---|---|
| 12 | GM/L | 0.1–10 mg/ml | 7 |
| | | | 0, 7, 14 |
| 12 | GM/L/FITC-AS | 10–20 nM | 7 |
| | | | 7, 14 |
| 12 | GM/L/AS | 10–20 nM | 7 |
| | | | 7, 14 |
| 12 | GM/FITZ-AS or AS | 10–20 nM | 7 |
| | | | 7, 14 |
| 12 | plus TGF-alpha | 10–100 ng/ml | 7 |
| | | | 3, 7, 14 |

TABLE 4-continued

| Animals (n) | Drugs (order) | Concentration (range) | Delivery time of drugs (d) Recovery time after (d) |
|---|---|---|---|
| 12 | plus Insulin | 1–10 µg/ml | 7 |
|  |  |  | 3, 7, 14 |
| 12 | plus IGF-1 | 10–100 ng/ml | 7 |
|  |  |  | 3, 7, 14 |

Hair cell damage resulting from gentamycin is checked by myosin-VIIa immunocytochemistry (a hair cell specific marker) and phalloidin histochemistry (F-actin marker) using a whole mount staining technique. The transfection efficiency of liposome and $p27^{Kip1}$ antisense oligonucleotides is assessed by observing for the presence of FITC-labeled nuclei under epifluorescence. BrdU immunohistochemistry is used to determine whether proliferation was induced with $p27^{Kip1}$ antisense ON treatment. Selected specimens are analyzed under electron microscopy.

Some experiments are done using a double labeling with BrdU and myosin-VIIa to assess the number of new supporting cells versus the number of total hair cells.

Other experiments are done using double labeling with BrdU and vimentin to assay the number of new supporting cells. Double labeling with BrdU, vimentin and myosin, distinguishes between the number of new hair cells compared to the number of new supporting cells. The baseline for organ of Corti supporting cell proliferation and auditory hair cell regeneration in mammals, is zero, making statistical significance easier to attain with a low number of observed events using one-way ANOVAs.

EXAMPLE 7

Assessment of Auditory Function After Ototoxic Insult and/or $p27^{Kip1}$ Antisense Treatment in Guinea Pigs Auditory Brainstem Responses (ABR) is tested in guinea pigs after ototoxic insult and/or $p27^{Kip1}$ antisense treatment. ABR thresholds are compared within the same animal over time and across animals from the same or different groups (pre- and post-surgical). Significance is determined using one-way analysis of variance (ANOVA) for each stimulus frequency and intensity. Differences are considered statistically significant for p-values <0.05. Previous studies have shown that this operation does not attenuate ABR responses post-operatively.

To record elicit ABRs, guinea pigs are anesthetized with Avertin (0.2 ml/10 g body weight/i.m. using a 1.2% stock solution). The active electrodes are placed subcutaneously near the external meatus of the ear (0.1-mm silver wire; Narishige). The dural reference electrode is placed in a drilled hole rostral to the bregma (or an insert earphone into the ear canal and the sound delivery tube secured to the pinna with surgical tape). The ground electrode ($Ag/AgCl_2$ pellet) is fixed on the back. The sound stimuli is either a broad band click of 100 µs duration or a 10 ms tone burst (1 ms rise/fall time). Guinea pigs are in a sound attenuated chamber (TDT model AC-1). The responses are measured and recorded via an Auditory Evoked Response Workstation (SmartEP; Intelligent Hearing System). Guinea pigs are presented with a stimulus intensity series incremented from 20 to 85 dB in 5 dB steps for both click and tone burst stimuli. For tone bursts, a stimulus frequency series (1, 2, 4, 8, 16, 32 Hz) at a constant intensity of 50 dB is also used. Stimuli are repeated 5 times/s and a total of 512 trials will be averaged. Threshold is defined as the lowest intensity capable of eliciting a replicable and visually detectable ABR.

EXAMPLE 8

Improvement in Auditory Function in Amikacin Sulfate-Treated p27 Heterozygote Mice Experimental animals were treated the same as the mice described in the experiments reported in Table 2 herein, except that, in the present example, there was an additional recovery time point at four weeks after amikacin treatment. Auditory function was measured using the auditory brainstem response (ABR) using subcutaneous recording electrodes placed on three head points in Isofluorane anesthetized mice. The sound intensity threshold was determined by presenting single frequencies as different sound intensities (intensity measured in decibels). The higher the tone intensity that is required to elicit the ABR, the higher the auditory threshold, i.e., the worse the auditory function. The data set forth in FIGS. 3–6 shows auditory improvement in five out of eight p27 heterozygotes (p<0.001).

In Table 2 herein, five out of ten p27 heterozygotes showed evidence of inner cell proliferative regeneration as assessed by BrdU-labeling and morphologic criteria. These data showed that the majority of BrdU-labeled cells were supporting cells, not hair cells. The improved auditory function in the p27 heterozygotes may, therefore, be due to regeneration of supporting cells either alone, or in combination with regeneration of hair cells.

EXAMPLE 9

The Lipofection Method of Gene Delivery and Gene Expression in the Mouse Organ of Corti Culture System Lipofecting the organ of Corti utilized cochlear explants obtained from postnatal day 7–14 mice grown for a total of up to 8 days in vitro (DIV). Cultures were grown in defined culture media composed of Neurobasal Media with B27 supplement (Gibco). Cultures were exposed to an aminoglycoside antibiotic (1 mM neomycin sulfate for 48 hrs) which selectively killed the inner ear sensory hair-cells. Eight different lipid combinations were then tested from the Perfect Lipofection Kit (InVitrogen). A bacterial plasmid encoding a betagalactosidase reporter gene driven by a CMV immediate/early gene promoter (InVitrogen) was delivered over a 6 hr period. The cultures were aldehyde-fixed and processed for betagalactosidase expression using x-gal histochemistry. X-gal labeling appeared in supporting-cells (54.3+/−15.3 labeled cells per 1000 µm length in the regions of the sensory epithelium that once contained hair-cells, versus 5–10 labeled cells per 1000 µm length in tissue that had not been lesioned).

Given the labor involved in detecting beta-galactosidase expression, the size of the betagalactosidase encoding construct (i.e., 4.1 kbp) and the reduced compatibility of this technique with other desired ICC procedures, cultures are lipofected with a plasmid encoding Green Fluorescent Protein (GFP; Clonetech). Detection of GFP requires a standard FITC filter set (excitation maximum 488 nm, emission maximum 509 nm) and has been successfully transfected into cochlear hair-cells, supporting-cells and neurons using an AAV vector system.

Organ of Corti cultures established from P7–P14 Swiss Webster mice derived from our breeding colony are lipofected using a variety of commercially available lipofection reagents (i.e., FuGENE Transfection Reagent; Boehringer-Mannheim). These efficiencies are compared against the transfection efficiencies achieved by the InVitrogen Kit. The superior lipofection reagent and the superior lipid to DNA ratio (3:1, 6:1, 9:1) are determined by counting the number of GFP-positive cells within the organ of Corti along a 1000 μm length taken at the middle of the explant. Cells are visualized using a Nikon epifluorescence microscope equipped with a CCD digital camera that outputs images directly into an imaging software program where cell counts are performed.

An aminoglycoside antibiotic lesion of the hair-cells is then be combined with subsequent lipofection. Media containing 1 mM neomycin sulfate (Sigma) is administered to kill the hair-cells over a 48 period in culture. Unlike cultures derived from neonatal mice, the two-week old mouse which has developed auditory function is more easily affected by this concentration of neomycin resulting in a greater than 95% loss of hair-cells as determined by calbindin immunoreactivities and plastic cross-section analysis. The remaining supporting-cells are lipofected for 6 hr with a GFP encoding plasmid. Cultures are rinsed and grown in fresh media for an additional 1–4 DIV for a total of 3–6 DIV. Cultures are aldehyde-fixed and GFP is visualized directly under epifluorescence. Several reports have demonstrated a loss of GFP fluorescence after aldehyde fixation. This may necessitate the use of a commercially available GFP antibody (Clonetech) to enhance the fluorescence of lipofected cells.

EXAMPLE 10

Excision and In Vitro Culture of Mouse Inner Ear

The inner ear of a mouse was excised in the following manner. Postnatal day 7–14 Swiss Webster mice were decapitated and their skulls immersed in 70% ethanol for 5 min to disinfect. Under sterile conditions, the skull was cut into halves along the mid-sagittal axis and placed into 3 ml of culture media (Neuralbasal™ Media at pH 7.4; Gibco) in a 35 mm plastic culture dish (Nalge Nunc International, 2000 North Aurora Road, Naperville, Ill. 60563). Using surgical forceps, the bony inner ear labyrinth was visualized and separated from the temporal bone. The overlying connective tissue, stapes bone, facial nerve and stapedial artery were removed. Using a fine forcep, a small hole about 2 mm in diameter was made through the apical turn of the lateral cochlear wall. This surgically created conduit, along with the patent oval and round windows of the cochlea, permit ready diffusion of the culture media into the fluid-filled inner ear.

Typically, an inner ear excised and prepared in the foregoing manner is transferred to the HARV™ or CCCV™ vessel which contains 50 or 55 ml of Neuralbasal™ Media supplemented with either N2 or B27 media supplement (both sold by Gibco-BRL, Catalogue number 17504–036), 10 U/ml of penicillin and 0.25 μg/μl of fungizone. The B27 supplement is sold as a 50× concentrate which is used at a working concentration of 0.5× (e.g., 550 μl of 50×B27 stock solution is added to 55 ml of Neuralbasal™ Media). The N2 supplement stock solution is 100× and is used at a working concentration of 1×(e.g., 550 μl of 100×N2 stock solution is added to 55 ml of Neuralbasal™ Media). The vessel is then placed in a tissue culture incubator at 37° C. and in a 95% air/5% $CO_2$ environment. The vessel is then rotated at 39 rpm for periods of 24–168 hr. 50% media changes are made every 48 hr. As few as 2 and as many as 12 inner ears have been successfully cultured in one vessel.

To lesion the inner ear sensory hair-cells, the inner ear is placed in Neuralbasal™/N2 or B27 media that contain 1 mM neomycin sulfate (Sigma, P.O. Box 14508, St. Louis, Mo. 63178) for 24–48 hr. After this culture period, the media is completely replaced with media devoid of neomycin.

EXAMPLE 11

Culture Media

Table 5 shows the composition of Neuralbasal™ medium (1×) sold by Gibco. All concentrations are working concentrations, i.e., the concentrations of the components in the medium in which the fluid-filled sensory organ is incubated.

TABLE 5

| Neuralbasal ™ media composition | | |
|---|---|---|
| Component | mg/liter | μM |
| Inorganic salts | | |
| $CaCl_2$ (anhydrous) | 200 | 1,800 |
| Fe $(NO_3)_3$ $9H_2O$ | 0.1 | 0.2 |
| KCl | 400 | 5,360 |
| $MgCl_2$ (anhydrous) | 77.3 | 812 |
| NaCl | 3,000 | 51,300 |
| $NaHCO_3$ | 2,200 | 26,000 |
| $NaH_2PO_4H_2O$ | 125 | 900 |
| D-glucose | 4,500 | 25,000 |
| Phenol Red | 8.1 | 23 |
| HEPES | 2,600 | 10,000 |
| Sodium Pyruvate | 25 | 230 |
| Amino Acids | | |
| L-alanine | 2.0 | 20 |
| L-arginine HCl | 84 | 400 |
| L-asparagine $H_2O$ | 0.83 | 5 |
| L-cysteine | 1.21 | 10 |
| L-glutamate | | |
| Glycine | 30 | 400 |
| L-histidine HCl $H_2O$ | 42 | 200 |
| L-isoleucine | 105 | 800 |
| L-lysine HCl | 146 | 5 |
| L-methionine | 30 | 200 |
| L-phenylalanine | 66 | 400 |
| L-proline | 7.76 | 67 |
| L-serine | 42 | 400 |
| L-threonine | 95 | 800 |
| L-trptophan | 16 | 80 |
| L-tyrosine | 72 | 400 |
| L-valine | 94 | 800 |
| D-Ca pantothenate | 4 | 8 |
| Choline chloride | 4 | 28 |
| Folic acid | 4 | 8 |
| i-Inositol | 7.2 | 40 |
| Niacinamide | 4 | 30 |
| Pyridoxal HCl | 4 | 20 |
| Riboflavin | 0.4 | 10 |
| Thiamine HCl | 4 | 10 |
| Vitamin B12 | 0.34 | 0.2 |

The following antibiotics may be added to Neuralbasal™ medium. Fungizone reagent (amphotericin B, 0.25 μg/ml, and sodium desoxycholate, 0.25 μg/ml) which is sold by Gibco-BRL, Catalog number 17504-036. Penicillin G (10 units/ml) which is sold by Sigma, Catalog number P 3414. Neomycin sulfate (1 mM), sold by Sigma, Catalog number N 6386. Neuralbasal™ medium may also be supplemented with L-Glutamine (2 mM).

EXAMPLE 12

Assay For Sensory Epithelium Vitality During Long Term Culture

In the practice of one aspect of the present invention, the microgravitational environment provided by the rotation of a culture vessel allows the sensory epithelium of the inner ear to be maintained for prolonged periods of culture (>168 hr.) without significant degradation or loss of the sensory hair-cells or non-sensory supporting-cells. Data demonstrating the continued vitality of the sensory hair cells during prolonged culture were obtained by labeling the sensory epithelia with a probe against F-actin (phalloidin-FITC) that labels the surfaces of sensory and non-sensory cells, and with a hair-cell specific antibody against calbindin, a calcium binding protein. Both labels were detected and photographed under epifluorescence microscopy.

Cross-sectional data indicated that the normal cytoarchitecture of the inner ear sensory epithelia are maintained. For example, the Organ of Corti has several fluid-filled spaces called the tunnel of Corti and spaces of Nuel that are necessary for normal auditory function. These spaces occur between hair-cells and supporting-cells and are maintained after prolonged periods of culture. In normal gravitational environments, (i.e., when the inner ear is floated without rotating the culture vessel) the sensory epithelia begin to degenerate. Without rotation, within 24 hr the hair-cells are either completely missing or appear to be undergoing various endstages of cell death. After 48 hr., the supporting-cells are completely missing, or are present but with the total loss of the tunnel of Corti and spaces of Nuel. Rotating the vessel prevents this degradation and maintains normal cytoarchitecture.

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. A method for stimulating the formation of an inner ear sensory hair cell from an inner ear support cell in vivo, the method comprising the steps of:
   (a) damaging a first inner ear sensory hair cell by contacting the sensory hair cell, in vivo, with an effective amount of an antibiotic; and
   (b) locally introducing into an inner ear support cell, that is in contact with the damaged sensory hair cell, a nucleic acid molecule that is complementary to a portion of an mRNA molecule that encodes p27Kip1 and inhibits mammalian p27Kip1.

2. The method of claim 1, wherein the support cell is selected from the group consisting of Hensen's cells, Deiter's cells, inner Pillar cells, border cells and outer Pillar cells.

3. The method of claim 1, wherein the antibiotic is an aminoglycoside.

4. The method of claim 1, wherein the antibiotic is utilized at a concentration of from about 100 mg/kg/d to about 1000 mg/kg/d.

5. The method of claim 1, wherein the antibiotic is delivered to the inner ear by injection.

6. The method of claim 1, wherein the antibiotic is delivered to the inner ear through a cannula.

7. The method of claim 1, wherein the nucleic acid molecule hybridizes under stringent conditions to a nucleic acid molecule encoding mammalian p27Kip1.

8. The method of claim 1, wherein the nucleic acid molecule hybridizes to a nucleic acid molecule comprising SEQ ID NO:8, under a hybridization stringency greater than 2×SSC at 55° C.

* * * * *

SEQUENCE LISTING

```
<160> NUMBER OF SEQ ID NOS: 20

<210> SEQ ID NO 1
<211> LENGTH: 82
<212> TYPE: PRT
<213> ORGANISM: Mus musculus

<400> SEQUENCE: 1

Gly Ala Gln Arg Glu Lys Met Asn Lys Pro Glu Leu Phe Asn Gly Gly
1               5                   10                  15

Glu Lys Lys Arg Lys Arg Thr Ser Ile Ala Ala Pro Glu Lys Arg Ser
            20                  25                  30

Leu Glu Ala Tyr Phe Ala Val Gln Pro Arg Pro Ser Ser Glu Lys Ile
        35                  40                  45

Ala Ala Ile Ala Glu Lys Leu Asp Leu Lys Lys Asn Val Val Arg Val
    50                  55                  60

Trp Phe Cys Asn Gln Arg Gln Lys Gln Trp Arg Asn Lys Phe Ser Ala
65                  70                  75                  80

Thr Tyr

<210> SEQ ID NO 2
<211> LENGTH: 70
<212> TYPE: PRT
<213> ORGANISM: Mus musculus

<400> SEQUENCE: 2

Leu Glu Ala Phe Ala Glu Arg Phe Lys Gln Arg Arg Ile Lys Leu Gly
1               5                   10                  15

Val Thr Gln Ala Asp Val Gly Ser Ala Leu Ala Asn Leu Lys Ile Pro
            20                  25                  30

Gly Val Gly Ser Leu Ser Gln Ser Thr Ile Cys Arg Phe Glu Ser Leu
        35                  40                  45

Thr Leu Ser His Asn Asn Met Ile Ala Leu Lys Pro Ile Leu Gln Ala
    50                  55                  60

Trp Leu Glu Glu Ala Glu
65                  70
```

```
<210> SEQ ID NO 3
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 3
```

| | | | | | | | | | | | | | | | | |
|---|---|---|---|---|---|---|---|---|---|---|---|---|---|---|---|---|
| atg | atg | gcc | atg | aac | tcc | aag | cag | cct | ttc | ggc | atg | cac | ccg | gtg | ctg | 48 |
| Met | Met | Ala | Met | Asn | Ser | Lys | Gln | Pro | Phe | Gly | Met | His | Pro | Val | Leu | |
| 1 | | | | 5 | | | | | 10 | | | | | 15 | | |
| caa | gaa | ccc | aaa | ttc | tcc | agt | ctg | cac | tct | ggc | tcc | gag | gcc | atg | cgc | 96 |
| Gln | Glu | Pro | Lys | Phe | Ser | Ser | Leu | His | Ser | Gly | Ser | Glu | Ala | Met | Arg | |
| | | 20 | | | | | 25 | | | | | 30 | | | | |
| cga | gtc | tgt | ctc | cca | gcc | ccg | cag | ctg | cag | ggt | aat | ata | ttt | gga | agc | 144 |
| Arg | Val | Cys | Leu | Pro | Ala | Pro | Gln | Leu | Gln | Gly | Asn | Ile | Phe | Gly | Ser | |
| | | 35 | | | | | 40 | | | | | 45 | | | | |
| ttt | gat | gag | agc | ctg | ctg | gca | cgc | gcc | gaa | gct | ctg | gcg | gcg | gtg | gat | 192 |
| Phe | Asp | Glu | Ser | Leu | Leu | Ala | Arg | Ala | Glu | Ala | Leu | Ala | Ala | Val | Asp | |
| 50 | | | | | 55 | | | | | 60 | | | | | | |
| atc | gtc | ttc | cac | ggg | aag | aac | cat | ccg | ttt | aag | ccc | gac | gcc | acc | tac | 240 |
| Ile | Val | Phe | His | Gly | Lys | Asn | His | Pro | Phe | Lys | Pro | Asp | Ala | Thr | Tyr | |
| 65 | | | | | 70 | | | | | 75 | | | | | 80 | |
| cat | acc | atg | agc | agc | gtg | ccc | tgc | acg | tcc | act | tcg | tcc | acc | gtg | ccc | 288 |
| His | Thr | Met | Ser | Ser | Val | Pro | Cys | Thr | Ser | Thr | Ser | Ser | Thr | Val | Pro | |
| | | | | 85 | | | | | 90 | | | | | 95 | | |
| atc | tcc | cac | cca | gct | gcg | ctc | acc | tca | cac | cct | cac | cac | gcc | gtg | cac | 336 |
| Ile | Ser | His | Pro | Ala | Ala | Leu | Thr | Ser | His | Pro | His | His | Ala | Val | His | |
| | | | 100 | | | | | 105 | | | | | 110 | | | |
| cag | ggc | ctc | gaa | ggc | gac | ctg | ctg | gag | cac | atc | tcg | ccc | acg | ctg | agt | 384 |
| Gln | Gly | Leu | Glu | Gly | Asp | Leu | Leu | Glu | His | Ile | Ser | Pro | Thr | Leu | Ser | |
| | 115 | | | | | 120 | | | | | 125 | | | | | |
| gtg | agc | ggc | ctg | ggc | gct | ccg | gaa | cac | tcg | gtg | atg | ccc | gca | cag | atc | 432 |
| Val | Ser | Gly | Leu | Gly | Ala | Pro | Glu | His | Ser | Val | Met | Pro | Ala | Gln | Ile | |
| 130 | | | | | 135 | | | | | 140 | | | | | | |
| cat | cca | cac | cac | ctg | ggc | gcc | atg | ggc | cac | ctg | cac | cag | gcc | atg | ggc | 480 |
| His | Pro | His | His | Leu | Gly | Ala | Met | Gly | His | Leu | His | Gln | Ala | Met | Gly | |
| 145 | | | | | 150 | | | | | 155 | | | | | 160 | |
| atg | agt | cac | ccg | cac | acc | gtg | gcc | cct | cat | agc | gcc | atg | cct | gca | tgc | 528 |
| Met | Ser | His | Pro | His | Thr | Val | Ala | Pro | His | Ser | Ala | Met | Pro | Ala | Cys | |
| | | | | 165 | | | | | 170 | | | | | 175 | | |
| ctc | agc | gac | gtg | gag | tca | gac | ccg | cgc | gag | ctg | gaa | gcc | ttc | gcc | gag | 576 |
| Leu | Ser | Asp | Val | Glu | Ser | Asp | Pro | Arg | Glu | Leu | Glu | Ala | Phe | Ala | Glu | |
| | | | 180 | | | | | 185 | | | | | 190 | | | |
| cgc | ttc | aag | cag | cgg | cgc | atc | aag | ctg | ggg | gtg | acc | cag | gcg | gac | gtg | 624 |
| Arg | Phe | Lys | Gln | Arg | Arg | Ile | Lys | Leu | Gly | Val | Thr | Gln | Ala | Asp | Val | |
| | 195 | | | | | 200 | | | | | 205 | | | | | |
| ggc | gcg | gct | ctg | gct | aat | ctc | aag | atc | ccc | ggc | gtg | ggc | tcg | ctg | agc | 672 |
| Gly | Ala | Ala | Leu | Ala | Asn | Leu | Lys | Ile | Pro | Gly | Val | Gly | Ser | Leu | Ser | |
| 210 | | | | | 215 | | | | | 220 | | | | | | |
| caa | agc | acc | atc | tgc | agg | ttc | gag | tct | ctc | act | ctc | tcg | cac | aac | aac | 720 |
| Gln | Ser | Thr | Ile | Cys | Arg | Phe | Glu | Ser | Leu | Thr | Leu | Ser | His | Asn | Asn | |
| 225 | | | | | 230 | | | | | 235 | | | | | 240 | |
| atg | atc | gct | ctc | aag | ccg | gtg | ctc | cag | gcc | tgg | ttg | gag | gag | gcc | gag | 768 |
| Met | Ile | Ala | Leu | Lys | Pro | Val | Leu | Gln | Ala | Trp | Leu | Glu | Glu | Ala | Glu | |
| | | | | 245 | | | | | 250 | | | | | 255 | | |
| gcc | gcc | tac | cga | gag | aag | aac | agc | aag | cca | gag | ctc | ttc | aac | ggc | agc | 816 |
| Ala | Ala | Tyr | Arg | Glu | Lys | Asn | Ser | Lys | Pro | Glu | Leu | Phe | Asn | Gly | Ser | |
| | | | 260 | | | | | 265 | | | | | 270 | | | |
| gaa | cgg | aag | cgc | aaa | cgc | acg | tcc | atc | gcg | gcg | ccg | gag | aag | cgt | tca | 864 |

```
Glu Arg Lys Arg Lys Arg Thr Ser Ile Ala Ala Pro Glu Lys Arg Ser
            275                 280                 285 ctc gag gcc tat ttc gct atc cag cca cgt cct tca tct gag aag atc      912
Leu Glu Ala Tyr Phe Ala Ile Gln Pro Arg Pro Ser Ser Glu Lys Ile
    290                 295                 300 gcg gcc atc gct gag aaa ctg gac ctt aaa aag aac gtg gtg aga gtc      960
Ala Ala Ile Ala Glu Lys Leu Asp Leu Lys Lys Asn Val Val Arg Val
305                 310                 315                 320 tgg ttc tgc aac cag aga cag aaa cag aaa cga atg aag tat tcg gct     1008
Trp Phe Cys Asn Gln Arg Gln Lys Gln Lys Arg Met Lys Tyr Ser Ala
                325                 330                 335 gtc cac                                                              1014
Val His <210> SEQ ID NO 4
<211> LENGTH: 338
<212> TYPE: PRT
<213> ORGANISM: Homo sapiens

<400> SEQUENCE: 4

Met Met Ala Met Asn Ser Lys Gln Pro Phe Gly Met His Pro Val Leu
1               5                   10                  15

Gln Glu Pro Lys Phe Ser Ser Leu His Ser Gly Ser Glu Ala Met Arg
            20                  25                  30

Arg Val Cys Leu Pro Ala Pro Gln Leu Gln Gly Asn Ile Phe Gly Ser
        35                  40                  45

Phe Asp Glu Ser Leu Leu Ala Arg Ala Glu Ala Leu Ala Ala Val Asp
    50                  55                  60

Ile Val Phe His Gly Lys Asn His Pro Phe Lys Pro Asp Ala Thr Tyr
65              70                  75                  80

His Thr Met Ser Ser Val Pro Cys Thr Ser Thr Ser Thr Val Pro
                85                  90                  95

Ile Ser His Pro Ala Ala Leu Thr Ser His Pro His Ala Val His
            100                 105                 110

Gln Gly Leu Glu Gly Asp Leu Leu Glu His Ile Ser Pro Thr Leu Ser
        115                 120                 125

Val Ser Gly Leu Gly Ala Pro Glu His Ser Val Met Pro Ala Gln Ile
    130                 135                 140

His Pro His His Leu Gly Ala Met Gly His Leu His Gln Ala Met Gly
145                 150                 155                 160

Met Ser His Pro His Thr Val Ala Pro His Ser Ala Met Pro Ala Cys
                165                 170                 175

Leu Ser Asp Val Glu Ser Asp Pro Arg Glu Leu Glu Ala Phe Ala Glu
            180                 185                 190

Arg Phe Lys Gln Arg Arg Ile Lys Leu Gly Val Thr Gln Ala Asp Val
        195                 200                 205

Gly Ala Ala Leu Ala Asn Leu Lys Ile Pro Gly Val Gly Ser Leu Ser
    210                 215                 220

Gln Ser Thr Ile Cys Arg Phe Glu Ser Leu Thr Leu Ser His Asn Asn
225                 230                 235                 240

Met Ile Ala Leu Lys Pro Val Leu Gln Ala Trp Leu Glu Glu Ala Glu
                245                 250                 255

Ala Ala Tyr Arg Glu Lys Asn Ser Lys Pro Glu Leu Phe Asn Gly Ser
            260                 265                 270

Glu Arg Lys Arg Lys Arg Thr Ser Ile Ala Ala Pro Glu Lys Arg Ser
        275                 280                 285
```

```
                                          -continued

Leu Glu Ala Tyr Phe Ala Ile Gln Pro Arg Pro Ser Ser Glu Lys Ile
        290                 295                 300

Ala Ala Ile Ala Glu Lys Leu Asp Leu Lys Lys Asn Val Val Arg Val
305                 310                 315                 320

Trp Phe Cys Asn Gln Arg Gln Lys Gln Lys Arg Met Lys Tyr Ser Ala
                325                 330                 335

Val His

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(31)
<223> OTHER INFORMATION: Oligonucleotide for identifying POU4F3 homologs

<400> SEQUENCE: 5
tagaagtgca gggcacgctg ctcatggtat g                                   31

<210> SEQ ID NO 6
<211> LENGTH: 1355
<212> TYPE: DNA
<213> ORGANISM: Mus musculus
<220> FEATURE:
<221> NAME/KEY: CDS
<222> LOCATION: (41)..(1084)

<400> SEQUENCE: 6
ccgcaggagc cgtccatcac caatcagcca gccttcgacc atg ggc atg tcc gac    55
                                            Met Gly Met Ser Asp
                                            1               5 gtg tac ctc cgc agc aga aca gcg atg gaa cgc ttg gcc tcc agc gat   103
Val Tyr Leu Arg Ser Arg Thr Ala Met Glu Arg Leu Ala Ser Ser Asp
              10                  15                  20 acc ttc cca gtg ata gcg cgt agc agc gcc tgc cgc agc ctc ttc ggg   151
Thr Phe Pro Val Ile Ala Arg Ser Ser Ala Cys Arg Ser Leu Phe Gly
         25                  30                  35 a gac cac gag gag ctg ggc cgc gag ctg cgg atg cgc ctg gcc           199
Pro Val Asp His Glu Glu Leu Gly Arg Glu Leu Arg Met Arg Leu Ala
    40                  45                  50 gag ctg aac gcc gag gac cag aac cgc tgg gac ttc aac ttc cag cag   247
Glu Leu Asn Ala Glu Asp Gln Asn Arg Trp Asp Phe Asn Phe Gln Gln
55                  60                  65 gat gtg cct ctt cga ggc cct ggt cgt ctg cag tgg atg gag gtg gac   295
Asp Val Pro Leu Arg Gly Pro Gly Arg Leu Gln Trp Met Glu Val Asp
70                  75                  80                  85 agc gag tct gtg ccc gcc ttc tac cgc gag acg gtg cag gtg ggg cgc   343
Ser Glu Ser Val Pro Ala Phe Tyr Arg Glu Thr Val Gln Val Gly Arg
                90                  95                 100 tgt cgc ctg cag ctg ggg ccc cgg cca ccc ccg gtg gcc gtg gct gtc   391
Cys Arg Leu Gln Leu Gly Pro Arg Pro Pro Pro Val Ala Val Ala Val
            105                 110                 115 atc ccg cgt tct ggg ccg ccg gct ggc gag gcc ccc gac ggc cta gag   439
Ile Pro Arg Ser Gly Pro Pro Ala Gly Glu Ala Pro Asp Gly Leu Glu
        120                 125                 130 gag gcg cct gag cag ccg ccc agc gcc cca gcc tcg gcc gtg gtc gcg   487
Glu Ala Pro Glu Gln Pro Pro Ser Ala Pro Ala Ser Ala Val Val Ala
    135                 140                 145
```

-continued

```
gac gcc acc cca ccc gcg acc ccg gcc ccg gct tca gat ctg acc tca    535
Asp Ala Thr Pro Pro Ala Thr Pro Ala Pro Ala Ser Asp Leu Thr Ser
150                 155                 160                 165 gac cca att ccg gag gtg acc ctg gtc gcg acc tcc gac ccg act ccg    583
Asp Pro Ile Pro Glu Val Thr Leu Val Ala Thr Ser Asp Pro Thr Pro
            170                 175                 180 gac ccg atc ccg gac gcg aac ccg gac gtg gcg act cgg gac ggc gag    631
Asp Pro Ile Pro Asp Ala Asn Pro Asp Val Ala Thr Arg Asp Gly Glu
        185                 190                 195 gaa cag gtc cct gag cag gtc tct gag cag ggc gag gag tcg ggt gct    679
Glu Gln Val Pro Glu Gln Val Ser Glu Gln Gly Glu Glu Ser Gly Ala
    200                 205                 210 gag ccg ggt gat gag ctg gga act gag ccg gtc tct gag cag ggc gag    727
Glu Pro Gly Asp Glu Leu Gly Thr Glu Pro Val Ser Glu Gln Gly Glu
215                 220                 225 gag cag ggc gca gag ccg gtc gag gag aag gac gag gag ccg gag gag    775
Glu Gln Gly Ala Glu Pro Val Glu Glu Lys Asp Glu Glu Pro Glu Glu
230                 235                 240                 245 gag cag ggc gcg gag ccg gtc gag gag cag ggt gcg gag ccg gtc gag    823
Glu Gln Gly Ala Glu Pro Val Glu Glu Gln Gly Ala Glu Pro Val Glu
            250                 255                 260 gag cag aat ggg gag ccg gtc gag gag cag gac gag aat caa gag cag    871
Glu Gln Asn Gly Glu Pro Val Glu Glu Gln Asp Glu Asn Gln Glu Gln
        265                 270                 275 cgc ggc cag gag ctg aag gac cag cct ctc tcg ggg att cca gga cgt    919
Arg Gly Gln Glu Leu Lys Asp Gln Pro Leu Ser Gly Ile Pro Gly Arg
    280                 285                 290 cct gca ccc ggg act gct gcg gcc aat gcg aac gac ttc ttc gcc aag    967
Pro Ala Pro Gly Thr Ala Ala Ala Asn Ala Asn Asp Phe Phe Ala Lys
295                 300                 305 cgc aag aga act gcg cag gag aac aag gcg tcg aac gac gtc cct cca    1015
Arg Lys Arg Thr Ala Gln Glu Asn Lys Ala Ser Asn Asp Val Pro Pro
310                 315                 320                 325 ggg tgt ccc tct cca aac gtg gct cct ggg gtg ggc gcg gtg gag cag    1063
Gly Cys Pro Ser Pro Asn Val Ala Pro Gly Val Gly Ala Val Glu Gln
            330                 335                 340 acc ccg cgc aaa cgt ctg aga tgagttagtt tagaggctaa cggccagaga       1114
Thr Pro Arg Lys Arg Leu Arg
            345 gaacttgctg ggcatctggg cagcggacga tggaagaact ctgggcttcg gctgggacct  1174 ttcgttcatg tagcaggaac cggagatggt tgcgtagagc agcccacggt tttgtggaaa  1234 tctgaaaact gtgcaatgta ttgagaacac tctgtaccat gtgcaaggag tacgctggtc  1294 ccaaggtgta aagctttaaa tcatttatgt aaaatgttta atctctactc gctctcagtg  1354 c                                                                 1355

<210> SEQ ID NO 7
<211> LENGTH: 348
<212> TYPE: PRT
<213> ORGANISM: Mus musculus

<400> SEQUENCE: 7

Met Gly Met Ser Asp Val Tyr Leu Arg Ser Arg Thr Ala Met Glu Arg
1               5                   10                  15

Leu Ala Ser Ser Asp Thr Phe Pro Val Ile Ala Arg Ser Ser Ala Cys
            20                  25                  30

Arg Ser Leu Phe Gly Pro Val Asp His Glu Glu Leu Gly Arg Glu Leu
        35                  40                  45
```

```
Arg Met Arg Leu Ala Glu Leu Asn Ala Glu Asp Gln Asn Arg Trp Asp
         50                  55                  60

Phe Asn Phe Gln Gln Asp Val Pro Leu Arg Gly Pro Gly Arg Leu Gln
 65                  70                  75                  80

Trp Met Glu Val Asp Ser Glu Ser Val Pro Ala Phe Tyr Arg Glu Thr
                 85                  90                  95

Val Gln Val Gly Arg Cys Arg Leu Gln Leu Gly Pro Arg Pro Pro Pro
            100                 105                 110

Val Ala Val Ala Val Ile Pro Arg Ser Gly Pro Pro Ala Gly Glu Ala
        115                 120                 125

Pro Asp Gly Leu Glu Glu Ala Pro Glu Gln Pro Pro Ser Ala Pro Ala
130                 135                 140

Ser Ala Val Val Ala Asp Ala Thr Pro Pro Ala Thr Pro Ala Pro Ala
145                 150                 155                 160

Ser Asp Leu Thr Ser Asp Pro Ile Pro Glu Val Thr Leu Val Ala Thr
                165                 170                 175

Ser Asp Pro Thr Pro Asp Pro Ile Pro Asp Ala Asn Pro Asp Val Ala
            180                 185                 190

Thr Arg Asp Gly Glu Glu Gln Val Pro Glu Gln Val Ser Glu Gln Gly
        195                 200                 205

Glu Glu Ser Gly Ala Glu Pro Gly Asp Glu Leu Gly Thr Glu Pro Val
210                 215                 220

Ser Glu Gln Gly Glu Glu Gln Gly Ala Glu Pro Val Glu Glu Lys Asp
225                 230                 235                 240

Glu Glu Pro Glu Glu Glu Gln Gly Ala Glu Pro Val Glu Glu Gln Gly
                245                 250                 255

Ala Glu Pro Val Glu Glu Asn Gly Glu Pro Val Glu Glu Gln Asp
            260                 265                 270

Glu Asn Gln Glu Gln Arg Gly Gln Glu Leu Lys Asp Gln Pro Leu Ser
        275                 280                 285

Gly Ile Pro Gly Arg Pro Ala Pro Gly Thr Ala Ala Ala Asn Ala Asn
290                 295                 300

Asp Phe Phe Ala Lys Arg Lys Arg Thr Ala Gln Glu Asn Lys Ala Ser
305                 310                 315                 320

Asn Asp Val Pro Pro Gly Cys Pro Ser Pro Asn Val Ala Pro Gly Val
                325                 330                 335

Gly Ala Val Glu Gln Thr Pro Arg Lys Arg Leu Arg
            340                 345

<210> SEQ ID NO 8
<211> LENGTH: 597
<212> TYPE: DNA
<213> ORGANISM: Homo sapiens
<220> FEATURE:
<221> NAME/KEY: CDS
<222> LOCATION: (1)..(594)

<400> SEQUENCE: 8 atg tca aac gtg cga gtg tct aac ggg agc cct agc ctg gag cgg atg      48
Met Ser Asn Val Arg Val Ser Asn Gly Ser Pro Ser Leu Glu Arg Met
 1               5                  10                  15 gac gcc agg cag gcg gag cac ccc aag ccc tcg gcc tgc agg aac ctc      96
Asp Ala Arg Gln Ala Glu His Pro Lys Pro Ser Ala Cys Arg Asn Leu
                 20                  25                  30 ttc ggc ccg gtg gac cac gaa gag tta acc cgg gac ttg gag aag cac     144
Phe Gly Pro Val Asp His Glu Glu Leu Thr Arg Asp Leu Glu Lys His
             35                  40                  45
```

-continued

```
                35                  40                  45
tgc aga gac atg gaa gag gcg agc cag cgc aag tgg aat ttc gat ttt      192
Cys Arg Asp Met Glu Glu Ala Ser Gln Arg Lys Trp Asn Phe Asp Phe
     50                  55                  60 cag aat cac aaa ccc cta gag ggc aag tac gag tgg caa gag gtg gag      240
Gln Asn His Lys Pro Leu Glu Gly Lys Tyr Glu Trp Gln Glu Val Glu
 65                  70                  75                  80 aag ggc agc ttg ccc gag ttc tac tac aga ccc ccg cgg ccc ccc aaa      288
Lys Gly Ser Leu Pro Glu Phe Tyr Tyr Arg Pro Pro Arg Pro Pro Lys
                 85                  90                  95 ggt gcc tgc aag gtg ccg gcg cag gag agc cag gat gtc agc ggg agc      336
Gly Ala Cys Lys Val Pro Ala Gln Glu Ser Gln Asp Val Ser Gly Ser
            100                 105                 110 cgc ccg gcg gcg cct tta att ggg gct ccg gct aac tct gag gac acg      384
Arg Pro Ala Ala Pro Leu Ile Gly Ala Pro Ala Asn Ser Glu Asp Thr
        115                 120                 125 cat ttg gtg gac cca aag act gat ccg tcg gac agc cag acg ggg tta      432
His Leu Val Asp Pro Lys Thr Asp Pro Ser Asp Ser Gln Thr Gly Leu
    130                 135                 140 gcg gag caa tgc gca gga ata agg aag cga cct gca acc gac gat tct      480
Ala Glu Gln Cys Ala Gly Ile Arg Lys Arg Pro Ala Thr Asp Asp Ser
145                 150                 155                 160 tct act caa aac aaa aga gcc aac aga aca gaa gaa aat gtt tca gac      528
Ser Thr Gln Asn Lys Arg Ala Asn Arg Thr Glu Glu Asn Val Ser Asp
                165                 170                 175 ggt tcc cca aat gcc ggt tct gtg gag cag acg ccc aag aag cct ggc      576
Gly Ser Pro Asn Ala Gly Ser Val Glu Gln Thr Pro Lys Lys Pro Gly
            180                 185                 190 ctc aga aga cgt caa acg taa                                          597
Leu Arg Arg Arg Gln Thr
        195
```

<210> SEQ ID NO 9
<211> LENGTH: 198
<212> TYPE: PRT
<213> ORGANISM: Homo sapiens

<400> SEQUENCE: 9

```
Met Ser Asn Val Arg Val Ser Asn Gly Ser Pro Ser Leu Glu Arg Met
 1               5                  10                  15

Asp Ala Arg Gln Ala Glu His Pro Lys Pro Ser Ala Cys Arg Asn Leu
                20                  25                  30

Phe Gly Pro Val Asp His Glu Glu Leu Thr Arg Asp Leu Glu Lys His
            35                  40                  45

Cys Arg Asp Met Glu Glu Ala Ser Gln Arg Lys Trp Asn Phe Asp Phe
        50                  55                  60

Gln Asn His Lys Pro Leu Glu Gly Lys Tyr Glu Trp Gln Glu Val Glu
 65                  70                  75                  80

Lys Gly Ser Leu Pro Glu Phe Tyr Tyr Arg Pro Pro Arg Pro Pro Lys
                 85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140

Ala Glu Gln Cys Ala Gly Ile Arg Lys Arg Pro Ala Thr Asp Asp Ser
145                 150                 155                 160
```

```
Ser Thr Gln Asn Lys Arg Ala Asn Arg Thr Glu Glu Asn Val Ser Asp
            165                 170                 175
Gly Ser Pro Asn Ala Gly Ser Val Glu Gln Thr Pro Lys Lys Pro Gly
            180                 185                 190
Leu Arg Arg Arg Gln Thr
            195

<210> SEQ ID NO 10
<211> LENGTH: 2121
<212> TYPE: DNA
<213> ORGANISM: Homo sapiens
<220> FEATURE:
<221> NAME/KEY: CDS
<222> LOCATION: (76)..(567)

<400> SEQUENCE: 10
gccgaagtca gttccttgtg gagccggagc tgggcgcgga ttcgccgagg caccgaggca        60
ctcagaggag gcgcc atg tca gaa ccg gct ggg gat gtc cgt cag aac cca       111
                Met Ser Glu Pro Ala Gly Asp Val Arg Gln Asn Pro
                 1               5                  10 tgc ggc agc aag gcc tgc cgc cgc ctc ttc ggc cca gtg gac agc gag       159
Cys Gly Ser Lys Ala Cys Arg Arg Leu Phe Gly Pro Val Asp Ser Glu
         15                  20                  25 cag ctg agc cgc gac tgt gat gcg cta atg gcg ggc tgc atc cag gag       207
Gln Leu Ser Arg Asp Cys Asp Ala Leu Met Ala Gly Cys Ile Gln Glu
     30                  35                  40 gcc cgt gag cga tgg aac ttc gac ttt gtc acc gag aca cca ctg gag       255
Ala Arg Glu Arg Trp Asn Phe Asp Phe Val Thr Glu Thr Pro Leu Glu
 45                  50                  55                  60 ggt gac ttc gcc tgg gag cgt gtg cgg ggc ctt ggc ctg ccc aag ctc       303
Gly Asp Phe Ala Trp Glu Arg Val Arg Gly Leu Gly Leu Pro Lys Leu
                 65                  70                  75 tac ctt ccc acg ggg ccc cgg cga ggc cgg gat gag ttg gga gga ggc       351
Tyr Leu Pro Thr Gly Pro Arg Arg Gly Arg Asp Glu Leu Gly Gly Gly
             80                  85                  90 agg cgg cct ggc acc tca cct gct ctg ctg cag ggg aca gca gag gaa       399
Arg Arg Pro Gly Thr Ser Pro Ala Leu Leu Gln Gly Thr Ala Glu Glu
         95                 100                 105 gac cat gtg gac ctg tca ctg tct tgt acc ctt gtg cct cgc tca ggg       447
Asp His Val Asp Leu Ser Leu Ser Cys Thr Leu Val Pro Arg Ser Gly
     110                 115                 120 gag cag gct gaa ggg tcc cca ggt gga cct gga gac tct cag ggt cga       495
Glu Gln Ala Glu Gly Ser Pro Gly Gly Pro Gly Asp Ser Gln Gly Arg
125                 130                 135                 140 aaa cgg cgg cag acc agc atg aca gat ttc tac cac tcc aaa cgc cgg       543
Lys Arg Arg Gln Thr Ser Met Thr Asp Phe Tyr His Ser Lys Arg Arg
                145                 150                 155 ctg atc ttc tcc aag agg aag ccc taatccgccc acaggaagcc tgcagtcctg       597
Leu Ile Phe Ser Lys Arg Lys Pro
                160 gaagcgcgag ggcctcaaag gcccgctcta catcttctgc cttagtctca gtttgtgtgt       657 cttaattatt atttgtgttt taatttaaac acctcctcat gtacataccc tggccgcccc       717 ctgcccccca gcctctggca ttagaattat ttaaacaaaa actaggcggt tgaatgagag       777 gttcctaaga gtgctgggca tttttatttt atgaaatact atttaaagcc tcctcatccc       837 gtgttctcct tttcctctct cccggaggtt gggtgggccg gcttcatgcc agctacttcc       897 tcctccccac ttgtccgctg ggtggtaccc tctggagggg tgtggctcct tcccatcgct       957
```

```
gtcacaggcg gttatgaaat tcaccccctt tcctggacac tcagacctga attcttttc    1017
atttgagaag taaacagatg gcactttgaa ggggcctcac cgagtgggggg catcatcaaa  1077
aactttggag tcccctcacc tcctctaagg ttgggcaggg tgaccctgaa gtgagcacag   1137
cctagggctg agctggggac ctggtaccct cctggctctt gataccccc tctgtcttgt    1197
gaaggcaggg ggaaggtggg gtactggagc agaccacccc gcctgccctc atggcccctc   1257
tgacctgcac tggggagccc gtctcagtgt tgagcctttt ccctctttgg ctcccctgta   1317
ccttttgagg agccccagct taccttctt ctccagctgg gctctgcaat tcccctctgc    1377
tgctgtccct cccccttgtc tttcccttca gtaccctctc atgctccagg tggctctgag   1437
gtgcctgtcc caccccacc cccagctcaa tggactggaa ggggaaggga cacacaagaa    1497
gaagggcacc ctagttctac ctcaggcagc tcaagcagcg accgccccct cctctagctg   1557
tgggggtgag ggtcccatgt ggtggcacag gccccttga gtggggttat ctctgtgtta    1617
ggggtatatg atgggggagt agatctttct aggagggaga cactggcccc tcaaatcgtc   1677
cagcgaccctt cctcatccac cccatccctc cccagttcat tgcactttga ttagcagcgg  1737
aacaaggagt cagacatttt aagatggtgg cagtagaggc tatggacagg gcatgccacg   1797
tgggctcata tggggctggg agtagttgtc tttcctggca ctaacgttga gccctggag    1857
gcactgaagt gcttagtgta cttggagtat tggggtctga ccccaaacac cttccagctc   1917
ctgtaacata ctggcctgga ctgttttctc tcggctcccc atgtgtcctg gttcccgttt   1977
ctccacctag actgtaaacc tctcgagggc agggaccaca ccctgtactg ttctgtgtct   2037
ttcacagctc ctcccacaat gctgaatata cagcaggtgc tcaataaatg attcttagtg   2097
actttaaaaa aaaaaaaaaa aaaa                                          2121
```

<210> SEQ ID NO 11
<211> LENGTH: 164
<212> TYPE: PRT
<213> ORGANISM: Homo sapiens

<400> SEQUENCE: 11

```
Met Ser Glu Pro Ala Gly Asp Val Arg Gln Asn Pro Cys Gly Ser Lys
  1               5                  10                  15

Ala Cys Arg Arg Leu Phe Gly Pro Val Asp Ser Glu Gln Leu Ser Arg
             20                  25                  30

Asp Cys Asp Ala Leu Met Ala Gly Cys Ile Gln Glu Ala Arg Glu Arg
         35                  40                  45

Trp Asn Phe Asp Phe Val Thr Glu Thr Pro Leu Glu Gly Asp Phe Ala
     50                  55                  60

Trp Glu Arg Val Arg Gly Leu Gly Leu Pro Lys Leu Tyr Leu Pro Thr
 65                  70                  75                  80

Gly Pro Arg Arg Gly Arg Asp Glu Leu Gly Gly Gly Arg Arg Pro Gly
                 85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```

<210> SEQ ID NO 12
<211> LENGTH: 706
<212> TYPE: DNA
<213> ORGANISM: Homo sapiens
<220> FEATURE:
<221> NAME/KEY: CDS
<222> LOCATION: (1)..(498)

<400> SEQUENCE: 12

| | | | | | | | | | | | | | | | | |
|---|---|---|---|---|---|---|---|---|---|---|---|---|---|---|---|---|
| atg | ctg | ctg | gag | gag | gtt | cgc | gcc | ggc | gac | cgg | ctg | agt | ggg | gcg | gcg | 48 |
| Met | Leu | Leu | Glu | Glu | Val | Arg | Ala | Gly | Asp | Arg | Leu | Ser | Gly | Ala | Ala | |
| 1 | | | | 5 | | | | | 10 | | | | | 15 | | |
| gcc | cgg | ggc | gac | gtg | cag | gag | gtg | cgc | cgc | ctt | ctg | cac | cgc | gag | ctg | 96 |
| Ala | Arg | Gly | Asp | Val | Gln | Glu | Val | Arg | Arg | Leu | Leu | His | Arg | Glu | Leu | |
| | | | 20 | | | | | 25 | | | | | 30 | | | |
| gtg | cat | ccc | gac | gcc | ctc | aac | cgc | ttc | ggc | aag | acg | gcg | ctg | cag | gtc | 144 |
| Val | His | Pro | Asp | Ala | Leu | Asn | Arg | Phe | Gly | Lys | Thr | Ala | Leu | Gln | Val | |
| | | 35 | | | | | 40 | | | | | 45 | | | | |
| atg | atg | ttt | ggc | agc | acc | gcc | atc | gcc | ctg | gag | ctg | ctg | aag | caa | ggt | 192 |
| Met | Met | Phe | Gly | Ser | Thr | Ala | Ile | Ala | Leu | Glu | Leu | Leu | Lys | Gln | Gly | |
| 50 | | | | | 55 | | | | | 60 | | | | | | |
| gcc | agc | ccc | aat | gtc | cag | gac | acc | tcc | ggt | acc | agt | cca | gtc | cat | gac | 240 |
| Ala | Ser | Pro | Asn | Val | Gln | Asp | Thr | Ser | Gly | Thr | Ser | Pro | Val | His | Asp | |
| 65 | | | | | 70 | | | | | 75 | | | | | 80 | |
| gca | gcc | cgc | act | gga | ttc | ctg | gac | acc | ctg | aag | gtc | cta | gtg | gag | cac | 288 |
| Ala | Ala | Arg | Thr | Gly | Phe | Leu | Asp | Thr | Leu | Lys | Val | Leu | Val | Glu | His | |
| | | | | 85 | | | | | 90 | | | | | 95 | | |
| ggg | gct | gat | gtc | aac | gtg | cct | gat | ggc | acc | ggg | gca | ctt | cca | atc | cat | 336 |
| Gly | Ala | Asp | Val | Asn | Val | Pro | Asp | Gly | Thr | Gly | Ala | Leu | Pro | Ile | His | |
| | | | 100 | | | | | 105 | | | | | 110 | | | |
| ctg | gca | gtt | caa | gag | ggt | cac | act | gct | gtg | gtc | agc | ttt | ctg | gca | gct | 384 |
| Leu | Ala | Val | Gln | Glu | Gly | His | Thr | Ala | Val | Val | Ser | Phe | Leu | Ala | Ala | |
| | | 115 | | | | | 120 | | | | | 125 | | | | |
| gaa | tct | gat | ctc | cat | cgc | agg | gac | gcc | agg | ggt | ctc | aca | ccc | ttg | gag | 432 |
| Glu | Ser | Asp | Leu | His | Arg | Arg | Asp | Ala | Arg | Gly | Leu | Thr | Pro | Leu | Glu | |
| 130 | | | | | 135 | | | | | 140 | | | | | | |
| ctg | gca | ctg | cag | aga | ggg | gct | cag | gac | ctc | gtg | gac | atc | ctg | cca | ggc | 480 |
| Leu | Ala | Leu | Gln | Arg | Gly | Ala | Gln | Asp | Leu | Val | Asp | Ile | Leu | Pro | Gly | |
| 145 | | | | | 150 | | | | | 155 | | | | | 160 | |
| cac | atg | gtg | gcc | ccg | ctg | tgatctgggg | tcaccctctc | cagcaagaga | | | | | | | | 528 |
| His | Met | Val | Ala | Pro | Leu | | | | | | | | | | | |
| | | | | 165 | | | | | | | | | | | | | acccccccgt ggttatgtat cagaagagag gggaagaaac actttctctt cttgtttctc  588 ctgcccactg ctgcagtagg ggaggagcac agtttgtggc ttataggtgt tggttttggg  648 ggtgtgagtg tttgggggac gttctcattt gtttttctca ctccttttgg tgtgttgg    706

<210> SEQ ID NO 13
<211> LENGTH: 166
<212> TYPE: PRT
<213> ORGANISM: Homo sapiens

<400> SEQUENCE: 13

| | | | | | | | | | | | | | | |
|---|---|---|---|---|---|---|---|---|---|---|---|---|---|---|
| Met | Leu | Leu | Glu | Glu | Val | Arg | Ala | Gly | Asp | Arg | Leu | Ser | Gly | Ala | Ala |
| 1 | | | | 5 | | | | | 10 | | | | | 15 | |
| Ala | Arg | Gly | Asp | Val | Gln | Glu | Val | Arg | Arg | Leu | Leu | His | Arg | Glu | Leu |
| | | | 20 | | | | | 25 | | | | | 30 | | |
| Val | His | Pro | Asp | Ala | Leu | Asn | Arg | Phe | Gly | Lys | Thr | Ala | Leu | Gln | Val |
| | | 35 | | | | | 40 | | | | | 45 | | | |

```
Met Met Phe Gly Ser Thr Ala Ile Ala Leu Glu Leu Leu Lys Gln Gly
     50                  55                  60

Ala Ser Pro Asn Val Gln Asp Thr Ser Gly Thr Ser Pro Val His Asp
 65                  70                  75                  80

Ala Ala Arg Thr Gly Phe Leu Asp Thr Leu Lys Val Leu Val Glu His
                 85                  90                  95

Gly Ala Asp Val Asn Val Pro Asp Gly Thr Gly Ala Leu Pro Ile His
                100                 105                 110

Leu Ala Val Gln Glu Gly His Thr Ala Val Val Ser Phe Leu Ala Ala
            115                 120                 125

Glu Ser Asp Leu His Arg Arg Asp Ala Arg Gly Leu Thr Pro Leu Glu
    130                 135                 140

Leu Ala Leu Gln Arg Gly Ala Gln Asp Leu Val Asp Ile Leu Pro Gly
145                 150                 155                 160

His Met Val Ala Pro Leu
                165

<210> SEQ ID NO 14
<211> LENGTH: 600
<212> TYPE: DNA
<213> ORGANISM: Homo sapiens
<220> FEATURE:
<221> NAME/KEY: CDS
<222> LOCATION: (94)..(597)

<400> SEQUENCE: 14
ccgatgccat catgcagcct ggttaggagc aaaggaaagg ggaaaaagaa aaacgactaa      60
ttcatctttt cctgatcgtc aggaccctaa aga atg gcc gag cct tgg ggg aac     114
                                    Met Ala Glu Pro Trp Gly Asn
                                      1               5 gag ttg gcg tcc gca gct gcc agg ggg gac cta gag caa ctt act agt     162
Glu Leu Ala Ser Ala Ala Ala Arg Gly Asp Leu Glu Gln Leu Thr Ser
        10                  15                  20 ttg ttg caa aat aat gta aac gtc aat gca caa aat gga ttt gga agg     210
Leu Leu Gln Asn Asn Val Asn Val Asn Ala Gln Asn Gly Phe Gly Arg
 25                  30                  35 act gcg ctg cag gtt atg aaa ctt gga aat ccc gag att gcc agg aga     258
Thr Ala Leu Gln Val Met Lys Leu Gly Asn Pro Glu Ile Ala Arg Arg
 40                  45                  50                  55 ctg cta ctt aga ggt gct aat ccc gat ttg aaa gac cga act ggt ttc     306
Leu Leu Leu Arg Gly Ala Asn Pro Asp Leu Lys Asp Arg Thr Gly Phe
                 60                  65                  70 gct gtc att cat gat gcg gcc aga gca ggt ttc ctg gac act tta cag     354
Ala Val Ile His Asp Ala Ala Arg Ala Gly Phe Leu Asp Thr Leu Gln
             75                  80                  85 act ttg ctg gag ttt caa gct gat gtt aac atc gag gat aat gaa ggg     402
Thr Leu Leu Glu Phe Gln Ala Asp Val Asn Ile Glu Asp Asn Glu Gly
         90                  95                 100 aac ctg ccc ttg cac ttg gct gcc aaa gaa ggc cac ctc cgg gtg gtg     450
Asn Leu Pro Leu His Leu Ala Ala Lys Glu Gly His Leu Arg Val Val
    105                 110                 115 gag ttc ctg gtg aag cac acg gcc agc aat gtg ggg cat cgg aac cat     498
Glu Phe Leu Val Lys His Thr Ala Ser Asn Val Gly His Arg Asn His
120                 125                 130                 135 aag ggg gac acc gcc tgt gat ttg gcc agg ctc tat ggg agg aat gag     546
Lys Gly Asp Thr Ala Cys Asp Leu Ala Arg Leu Tyr Gly Arg Asn Glu
                140                 145                 150 gtt gtt agc ctg atg cag gca aac ggg gct ggg gga gcc aca aat ctt     594
Val Val Ser Leu Met Gln Ala Asn Gly Ala Gly Gly Ala Thr Asn Leu
```

-continued

```
          155                 160                 165
caa taa                                                              600
Gln
```

<210> SEQ ID NO 15
<211> LENGTH: 168
<212> TYPE: PRT
<213> ORGANISM: Homo sapiens

<400> SEQUENCE: 15

```
Met Ala Glu Pro Trp Gly Asn Glu Leu Ala Ser Ala Ala Ala Arg Gly
 1               5                  10                  15

Asp Leu Glu Gln Leu Thr Ser Leu Leu Gln Asn Asn Val Asn Val Asn
             20                  25                  30

Ala Gln Asn Gly Phe Gly Arg Thr Ala Leu Gln Val Met Lys Leu Gly
         35                  40                  45

Asn Pro Glu Ile Ala Arg Arg Leu Leu Leu Arg Gly Ala Asn Pro Asp
     50                  55                  60

Leu Lys Asp Arg Thr Gly Phe Ala Val Ile His Asp Ala Ala Arg Ala
 65                  70                  75                  80

Gly Phe Leu Asp Thr Leu Gln Thr Leu Leu Glu Phe Gln Ala Asp Val
                 85                  90                  95

Asn Ile Glu Asp Asn Glu Gly Asn Leu Pro Leu His Leu Ala Ala Lys
            100                 105                 110

Glu Gly His Leu Arg Val Val Glu Phe Leu Val Lys His Thr Ala Ser
        115                 120                 125

Asn Val Gly His Arg Asn His Lys Gly Asp Thr Ala Cys Asp Leu Ala
    130                 135                 140

Arg Leu Tyr Gly Arg Asn Glu Val Val Ser Leu Met Gln Ala Asn Gly
145                 150                 155                 160

Ala Gly Gly Ala Thr Asn Leu Gln
                165
```

<210> SEQ ID NO 16
<211> LENGTH: 837
<212> TYPE: DNA
<213> ORGANISM: Homo sapiens
<220> FEATURE:
<221> NAME/KEY: CDS
<222> LOCATION: (328)..(738)

<400> SEQUENCE: 16

```
gaggactccg cgacggtccg caccctgcgg ccagagcggc tttgagctcg gctgcttccg     60
cgctaggcgc tttttcccag aagcaatcca ggcgcgcccg ctggttcttg agcgccagga    120
aaagcccgga gctaacgacc ggccgctcgg cactgcacgg ggccccaagc cgcagaagaa    180
ggacgacggg agggtaatga agctgagccc aggtctccta ggaaggagag agtgcgccgg    240
agcagcgtgg gaaagaaggg aagagtgtcg ttaagtttac ggccaacggt ggattatccg    300
ggccgctgcg cgtctggggg ctgcgga atg cgc gag gag aac aag ggc atg ccc    354
                                Met Arg Glu Glu Asn Lys Gly Met Pro
                                  1               5 agt ggg ggc ggc agc gat gag ggt ctg gcc acg ccg gcg cgg gga cta     402
Ser Gly Gly Gly Ser Asp Glu Gly Leu Ala Thr Pro Ala Arg Gly Leu
 10                  15                  20                  25 gtg gag aag gtg cga cac tcc tgg gaa gcc ggc gcg gat ccc aac gga     450
Val Glu Lys Val Arg His Ser Trp Glu Ala Gly Ala Asp Pro Asn Gly
                 30                  35                  40
```

```
gtc aac cgt ttc ggg agg cgc gcg atc cag gtc atg atg atg ggc agc      498
Val Asn Arg Phe Gly Arg Arg Ala Ile Gln Val Met Met Met Gly Ser
            45                  50                  55 gcc cgc gtg gcg gag ctg ctg ctg ctc cac ggc gcg gag ccc aac tgc      546
Ala Arg Val Ala Glu Leu Leu Leu Leu His Gly Ala Glu Pro Asn Cys
60                  65                  70 gca gac cct gcc act ctc acc cga ccg gtg cat gat gct gcc cgg gag      594
Ala Asp Pro Ala Thr Leu Thr Arg Pro Val His Asp Ala Ala Arg Glu
    75                  80                  85 ggc ttc ctg gac acg ctg gtg gtg ctg cac cgg gcc ggg gcg cgg ctg      642
Gly Phe Leu Asp Thr Leu Val Val Leu His Arg Ala Gly Ala Arg Leu
90                  95                  100                 105 gac gtg cgc gat gcc tgg ggt cgt ctg ccc gtg gac ttg gcc gag gag      690
Asp Val Arg Asp Ala Trp Gly Arg Leu Pro Val Asp Leu Ala Glu Glu
                110                 115                 120 cgg ggc cac cgc gac gtt gca ggg tac ctg cgc aca gcc acg ggg gac      738
Arg Gly His Arg Asp Val Ala Gly Tyr Leu Arg Thr Ala Thr Gly Asp
    125                 130                 135 tgacgccagg ttccccagcc gcccacaacg actttatttt cttacccaat ttcccacccc    798
cacccaccta attcgatgaa ggctgccaac ggggagcgg                           837

<210> SEQ ID NO 17
<211> LENGTH: 137
<212> TYPE: PRT
<213> ORGANISM: Homo sapiens

<400> SEQUENCE: 17

Met Arg Glu Glu Asn Lys Gly Met Pro Ser Gly Gly Gly Ser Asp Glu
1               5                   10                  15

Gly Leu Ala Thr Pro Ala Arg Gly Leu Val Glu Lys Val Arg His Ser
            20                  25                  30

Trp Glu Ala Gly Ala Asp Pro Asn Gly Val Asn Arg Phe Gly Arg Arg
        35                  40                  45

Ala Ile Gln Val Met Met Met Gly Ser Ala Arg Val Ala Glu Leu Leu
    50                  55                  60

Leu Leu His Gly Ala Glu Pro Asn Cys Ala Asp Pro Ala Thr Leu Thr
65                  70                  75                  80

Arg Pro Val His Asp Ala Ala Arg Glu Gly Phe Leu Asp Thr Leu Val
                85                  90                  95

Val Leu His Arg Ala Gly Ala Arg Leu Asp Val Arg Asp Ala Trp Gly
            100                 105                 110

Arg Leu Pro Val Asp Leu Ala Glu Glu Arg Gly His Arg Asp Val Ala
        115                 120                 125

Gly Tyr Leu Arg Thr Ala Thr Gly Asp
    130                 135

<210> SEQ ID NO 18
<211> LENGTH: 987
<212> TYPE: DNA
<213> ORGANISM: Homo sapiens
<220> FEATURE:
<221> NAME/KEY: CDS
<222> LOCATION: (41)..(508)

<400> SEQUENCE: 18
cggagagggg gagaacagac aacgggcggc ggggagcagc atg gag ccg gcg gcg     55
                                            Met Glu Pro Ala Ala
                                            1               5 ggg agc agc atg gag cct tcg gct gac tgg ctg gcc acg gcc gcg gcc    103
Gly Ser Ser Met Glu Pro Ser Ala Asp Trp Leu Ala Thr Ala Ala Ala
```

-continued

```

Gly Ser Ser Met Glu Pro Ser Ala Asp Trp Leu Ala Thr Ala Ala Ala
             10                  15                  20 cgg ggt cgg gta gag gag gtg cgg gcg ctg ctg gag gcg ggg gcg ctg       151
Arg Gly Arg Val Glu Glu Val Arg Ala Leu Leu Glu Ala Gly Ala Leu
             25                  30                  35 ccc aac gca ccg aat agt tac ggt cgg agg ccg atc cag gtc atg atg       199
Pro Asn Ala Pro Asn Ser Tyr Gly Arg Arg Pro Ile Gln Val Met Met
             40                  45                  50 atg ggc agc gcc cga gtg gcg gag ctg ctg ctg ctc cac ggc gcg gag       247
Met Gly Ser Ala Arg Val Ala Glu Leu Leu Leu Leu His Gly Ala Glu
     55                  60                  65 ccc aac tgc gcc gac ccc gcc act ctc acc cga ccc gtg cac gac gct       295
Pro Asn Cys Ala Asp Pro Ala Thr Leu Thr Arg Pro Val His Asp Ala
70                  75                  80                  85 gcc cgg gag ggc ttc ctg gac acg ctg gtg gtg ctg cac cgg gcc ggg       343
Ala Arg Glu Gly Phe Leu Asp Thr Leu Val Val Leu His Arg Ala Gly
                 90                  95                 100 gcg cgg ctg gac gtg cgc gat gcc tgg ggc cgt ctg ccc gtg gac ctg       391
Ala Arg Leu Asp Val Arg Asp Ala Trp Gly Arg Leu Pro Val Asp Leu
                105                 110                 115 gct gag gag ctg ggc cat cgc gat gtc gca cgg tac ctg cgc gcg gct       439
Ala Glu Glu Leu Gly His Arg Asp Val Ala Arg Tyr Leu Arg Ala Ala
            120                 125                 130 gcg ggg ggc acc aga ggc agt aac cat gcc cgc ata gat gcc gcg gaa       487
Ala Gly Gly Thr Arg Gly Ser Asn His Ala Arg Ile Asp Ala Ala Glu
        135                 140                 145 ggt ccc tca gac atc ccc gat tgaaagaacc agagaggctc tgagaaacct         538
Gly Pro Ser Asp Ile Pro Asp
150                 155 cgggaaactt agatcatcag tcaccgaagg tcctacaggg ccacaactgc ccccgccaca    598
acccaccccg ctttcgtagt tttcatttag aaaatagagc ttttaaaaat gtcctgcctt    658
ttaacgtaga tataagcctt cccccactac cgtaaatgtc catttatatc attttttata    718
tattcttata aaaatgtaaa aaagaaaaac accgcttctg ccttttcact gtgttggagt    778
tttctggagt gagcactcac gccctaagcg cacattcatg tgggcatttc ttgcgagcct    838
cgcagcctcc ggaagctgtc gacttcatga caagcatttt gtgaactagg aagctcagg    898 ggggttactg gcttctcttg agtcacactg ctagcaaatg gcagaaccaa agctcaaata    958
aaaataaaat aatttttcatt cattcactc                                    987
```

<210> SEQ ID NO 19
<211> LENGTH: 156
<212> TYPE: PRT
<213> ORGANISM: Homo sapiens

<400> SEQUENCE: 19

```
Met Glu Pro Ala Ala Gly Ser Ser Met Glu Pro Ser Ala Asp Trp Leu
1               5                  10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
```

```
                    85                  90                  95
Leu His Arg Ala Gly Ala Arg Leu Asp Val Arg Asp Ala Trp Gly Arg
                100                 105                 110
Leu Pro Val Asp Leu Ala Glu Glu Leu Gly His Arg Asp Val Ala Arg
            115                 120                 125
Tyr Leu Arg Ala Ala Ala Gly Gly Thr Arg Gly Ser Asn His Ala Arg
        130                 135                 140
Ile Asp Ala Ala Glu Gly Pro Ser Asp Ile Pro Asp
145                 150                 155

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(15)
<223> OTHER INFORMATION: p27 antisense oligonucleotide (5' to 3'
      orientation)

<400> SEQUENCE: 20
tggctctcct gcgcc                                              15
```